US011426607B1

(12) United States Patent
Hara et al.

(10) Patent No.: US 11,426,607 B1
(45) Date of Patent: Aug. 30, 2022

(54) PATIENT SHUTTLE SYSTEM AND IRRADIATION SYSTEM FOR PARTICLE THERAPY

(71) Applicant: B dot Medical Inc., Tokyo (JP)

(72) Inventors: Yousuke Hara, Tokyo (JP); Yuka Matsuzaki, Tokyo (JP); Taishi Masuda, Tokyo (JP); Takuji Furukawa, Tokyo (JP)

(73) Assignee: B DOT MEDICAL INC., Tokyo (JP)

( * ) Notice: Subject to any disclaimer, the term of this patent is extended or adjusted under 35 U.S.C. 154(b) by 0 days.

(21) Appl. No.: 17/536,444

(22) Filed: Nov. 29, 2021

(30) Foreign Application Priority Data

Mar. 10, 2021  (JP) .............................. JP2021-038059

(51) Int. Cl.
*A61N 5/10* (2006.01)
*A61B 6/00* (2006.01)
*A61B 6/04* (2006.01)

(52) U.S. Cl.
CPC .......... *A61N 5/1069* (2013.01); *A61B 6/4405* (2013.01); *A61B 6/545* (2013.01);
(Continued)

(58) Field of Classification Search
CPC ........ A61N 5/10; A61N 5/103; A61N 5/1048; A61N 5/1049; A61N 5/1069; A61N 5/107;
(Continued)

(56) References Cited

U.S. PATENT DOCUMENTS

| 5,842,987 A * | 12/1998 | Sahadevan | ............... | A61B 6/04 600/407 |
| 6,640,364 B1 * | 11/2003 | Josephson | .............. | A61B 5/055 5/601 |

(Continued)

FOREIGN PATENT DOCUMENTS

| JP | 2007-7302 A | 1/2007 |
| JP | 2009-116667 A | 5/2009 |

(Continued)

OTHER PUBLICATIONS

Japanese Decision to Grant a Patent, issued in Priority Application No. 2021-038059, dated Jun. 1, 2021.
(Continued)

*Primary Examiner* — Anastasia Midkiff
(74) *Attorney, Agent, or Firm* — Birch, Stewart, Kolasch & Birch, LLP

(57) ABSTRACT

The invention provides a patient shuttle system and an irradiation system for particle therapy. A patient shuttle system of one embodiment of the invention includes: a patient table (110) adapted to carry a patient; a patient table drive unit (120) that moves and/or rotates the patient table; and a transfer unit (130) having a base (131) on which the patient table drive unit is placed. In a home position state of the patient shuttle system (100), the patient table and first and second arms of the patient table drive unit are configured to be folded in the height direction (Z-axis). A robot arm base connected to the second arm is fixed at a position off the center of the base in plan view, and thereby a helper space (135) where a helper may ride is secured on the base. The robot arm base is fixed in a recess (138) provided in the base.

9 Claims, 10 Drawing Sheets

(52) U.S. Cl.
CPC .............. *A61B 6/547* (2013.01); *A61B 6/548* (2013.01); *A61N 5/103* (2013.01); *A61N 5/107* (2013.01); *A61N 5/1048* (2013.01); *A61N 5/1049* (2013.01); *A61N 5/1083* (2013.01); *A61B 6/0487* (2020.08); *A61N 5/1081* (2013.01); *A61N 2005/1057* (2013.01); *A61N 2005/1059* (2013.01); *A61N 2005/1063* (2013.01); *A61N 2005/1085* (2013.01)

(58) Field of Classification Search
CPC .... A61N 2005/1041; A61N 2005/1057; A61N 2005/1059; A61N 2005/1063; A61N 2005/1083; A61B 6/04; A61B 6/0407; A61B 6/0487; A61B 6/0492; A61B 6/44; A61B 6/4405; A61B 6/4411; A61B 6/4417; A61B 6/54; A61B 6/542; A61B 6/545; A61B 6/547; A61B 6/548
See application file for complete search history.

(56) References Cited

U.S. PATENT DOCUMENTS

| | | | | |
|---|---|---|---|---|
| 6,782,571 | B1* | 8/2004 | Josephson | A61B 6/04 5/601 |
| 2010/0162488 | A1* | 7/2010 | Dahlin | A61B 6/04 378/209 |
| 2011/0066278 | A1 | 8/2011 | Pinault | |
| 2014/0034061 | A1 | 2/2014 | Marle et al. | |
| 2016/0184157 | A1* | 6/2016 | Hochman | A61G 13/10 5/600 |
| 2018/0085603 | A1 | 3/2018 | Kruesi et al. | |
| 2018/0177469 | A1 | 6/2018 | Suga | |
| 2019/0117809 | A1* | 4/2019 | Katz | G06T 7/50 |
| 2019/0298276 | A1 | 10/2019 | Pinault | |
| 2020/0306563 | A1* | 10/2020 | Hara | A61N 5/1079 |
| 2022/0104984 | A1 | 4/2022 | Keller et al. | |

FOREIGN PATENT DOCUMENTS

| | | |
|---|---|---|
| JP | 2009-207524 A | 9/2009 |
| JP | 2015-136444 A | 7/2015 |
| JP | 2018-122013 A | 8/2018 |
| JP | 6596679 B1 | 10/2019 |
| KR | 10-2016-0064329 A | 6/2016 |
| KR | 10-2080144 B1 | 2/2020 |
| WO | WO 2017/216075 A1 | 12/2017 |
| WO | WO 2020/143955 A1 | 7/2020 |

OTHER PUBLICATIONS

Notice of Allowance dated Jan. 10, 2022, in Republic of Korea Patent Application No. 10-2021-0159174.
English Translation of Notice of Allowance dated Jan. 10, 2022, in Republic of Korea Patent Application No. 10-2021-0159174.
Extended European Search Report for European Application No. 21210180.2, dated May 8, 2022.

\* cited by examiner

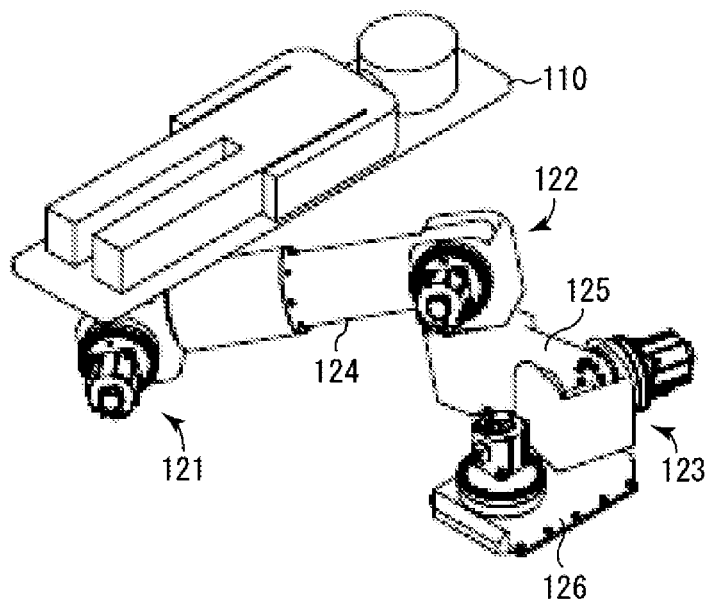
FIG.2a PATIENT BOADING POSITION
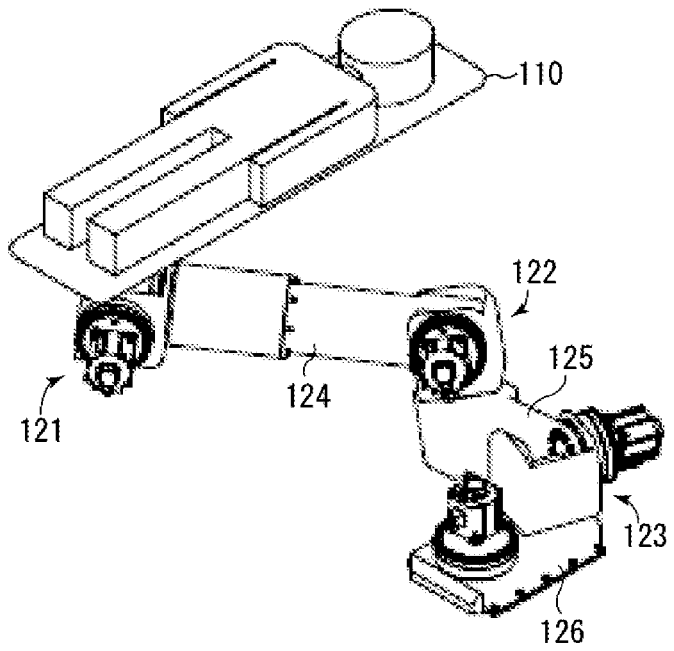
FIG.2b TREATMENT POSITION 1

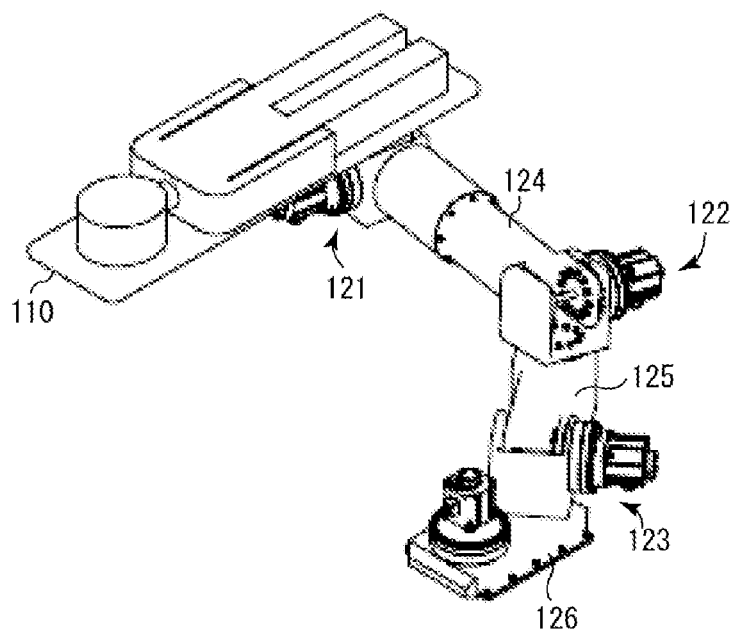
FIG.2c TREATMENT POSITION 2
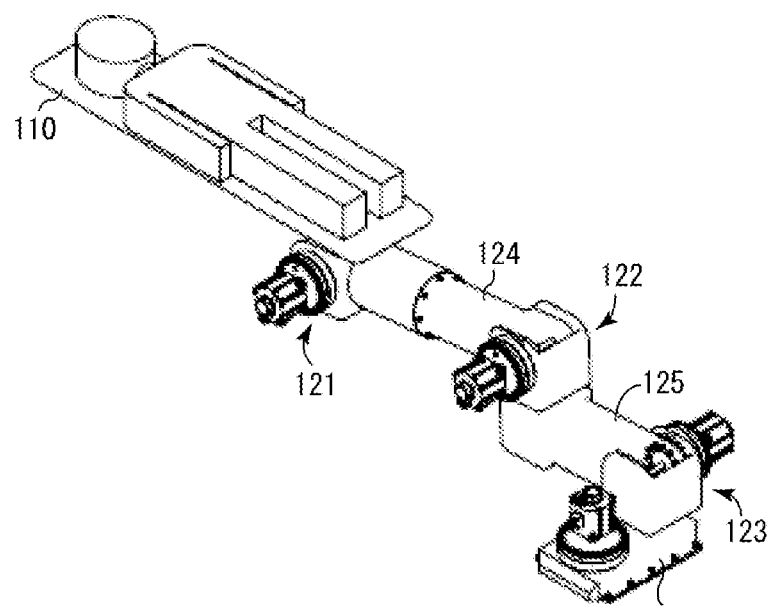
FIG.2d TREATMENT POSITION 3

PATIENT SHUTTLE SYSTEM AND IRRADIATION SYSTEM FOR PARTICLE THERAPY

BACKGROUND OF THE INVENTION

Field of the Invention

The present invention relates to a patient shuttle system and an irradiation system for particle therapy.

Description of the Related Art

In particle therapy, there have been treatment methods to irradiate a tumor part or the like such as a lesion or a cancer (a target) with a particle beam such as a proton beam, a heavy-ion beam, or a neutron beam extracted from an accelerator. To suppress a particle beam from affecting a normal tissue while concentrating the dose of the particle beam into a target, the particle beam is irradiated to the target at high accuracy.

Conventionally, before a particle beam is irradiated to a patient, a patient is placed on a treatment table placed on a room in which an irradiation nozzle for a particle beam is installed and particle therapy is performed (hereafter, referred to as "treatment room for particle therapy"), and the position of a particle beam irradiated from the irradiation nozzle and a site to be irradiated with the particle beam are then aligned with each other (referred to as a patient positioning process or a positioning process). That is, a particle beam irradiation position and a patient position are adjusted to each other so that the particle beam irradiated from an irradiation nozzle is irradiated to a target within a patient at high accuracy.

In a patient positioning process, first, to suppress displacement between a patient and a treatment table, the patient is secured to a patient table of the treatment table by using an immobilization device. Next, lasers or the like installed inside the treatment room for particle therapy are utilized to perform, from above the patient's skin, coarse alignment between a position to be irradiated with a particle beam and a site to be irradiated with a particle beam. An X-ray image, a CT image, or an MRI image of the patient is then acquired, the position, the posture, or the like of a patient table on which a patient is placed are adjusted with view of the acquired image, and a position to be irradiated with the particle beam is determined at high accuracy (for example, in the order of mm). After the patient positioning process, treatment using a particle beam is then started.

In general, a patient positioning process takes several minutes to several tens of minutes, and this process occupies most of irradiation time for particle therapy. A lengthy patient positioning process in a treatment room for particle therapy also increases occupancy time of the treatment room for particle therapy per patient. This results in a limited number of patients treated per unit time or results in tightened time to perform Quality Assurance (QA) measurement of a particle beam for ensuring safe therapy irradiation, which increases the burden on a medical worker such as a physician, a nurse, a radiologist, or the like.

Japanese Patent No. 6596679 discloses a technology to address a problem of displacement caused by transfer of a patient table on which a patient is placed to a treatment table installed in a treatment room for particle therapy, a problem of difficulty in installation of equipment used for QA measurement because a fixed treatment table stationarily installed in the treatment room for particle therapy increases the size of a treatment room for particle therapy, or the like. Japanese Patent No. 6596679 discloses a patient shuttle system having a patient table that carries a patient, a drive unit that translates and/or rotates the patient table, a drive control unit that controls translation and/or rotation of the patient table performed by the drive unit in accordance with a translation amount and/or a rotation amount of the patient table received from a patient positioning device provided in a treatment room for particle therapy, and a base lock mechanism that engages with a lock receiving part provided in the treatment room for particle therapy and fixes a patient shuttle system to the treatment room for particle therapy.

U.S. Pat. No. 9,554,953 discloses an omni-directional chassis that can move a medical device in any directions on a motion plane. The chassis of U.S. Pat. No. 9,554,953 has a configuration for changing the orientation of the medical device in some predetermined directions without rotating the same in order to change the moving direction of the medical device. Japanese Patent Application Laid-Open No. 2018-122013 discloses a technology that, for a treatment table having a conventional robot arm used for a patient positioning process and fixed to a treatment room, realizes a movable range of a patient table position where a patient easily gets on and off the patient table.

In the technology disclosed in Japanese Patent 6596679, an occupancy time of a treatment room for particle therapy is reduced, and the treatment efficiency is improved. However, since a patient is transferred to a treatment room for particle therapy while being secured on a patient table of a patient shuttle system, a helper such as a nurse may move together with the patient shuttle system for safety. In a hospital, a patient shuttle system is required to travel stably under circumstances where there are various obstacles, consideration for other patients or the like has to be taken, and there are slopes or the like. Further, the technology disclosed in Japanese Patent Application Laid-Open No. 2018-122013 relates to a fixed type treatment table embedded under the floor of a treatment room and requires a large-scale apparatus.

SUMMARY OF THE INVENTION

In view of such circumstances, the present invention intends to provide a patient shuttle system and an irradiation system for particle therapy.

The present invention includes the following aspects.

[1] A patient shuttle system (100) comprising:
a patient table (110) adapted to carry a patient;
a patient table drive unit (120) that moves and/or rotates the patient table; and
a transfer unit (130) having a base (131) on which the patient table drive unit is placed;
wherein the patient table drive unit comprises
a first rotating mechanism (121) connected to the patient table and configured to rotate the patient table,
a first arm (124) connected to the first rotating mechanism,
a second rotating mechanism (122) connected to the first arm and configured to rotate the first arm,
a second arm (125) connected to the second rotating mechanism,
a third rotating mechanism (123) connected to the second arm and configured to rotate the second arm, and
a robot arm base (126) connected to the third rotating mechanism,
wherein in a home position state of the patient shuttle system, the first rotating mechanism, the first arm, the second rotating mechanism, the second arm, the third rotating mechanism, and the robot arm base are configured to overlap the patient table in a height direction (Z-axis) such that the patient table, the first arm, and the second arm are in a folded state in the height direction (Z-axis), wherein the robot arm base is fixed at a position off the center of the base in plan view to secure, on the base, a helper space (135) where a helper is able to ride, and wherein the robot arm base is fixed in a recess (138) provided in the base.

[2] The patient shuttle system according to [1], wherein rotation about the Z-axis is defined as yaw rotation, an X-axis and a Y-axis orthogonal to each other are defined on a plane perpendicular to the Z-axis, rotation about the X-axis is defined as roll rotation, and rotation about the Y-axis is defined as pitch rotation, wherein the first rotating mechanism is configured to apply roll rotation, pitch rotation, and yaw rotation to the patient table, wherein the second rotating mechanism is configured to apply roll rotation and yaw rotation to the first arm, and wherein the third rotating mechanism is configured to apply roll rotation and yaw rotation to the second arm.

[3] The patient shuttle system according to [1] or [2], wherein three or more wheels (132) are mounted to the base, and the wheels are omni-directional drive wheels.

[4] A irradiation system for particle therapy (200) comprising:

the patient shuttle system according to any one of [1] to [3];

a particle beam irradiation apparatus (210) adapted to irradiate a patient with a particle beam; and a navigation controller (260) that controls traveling of the patient shuttle system, wherein the navigation controller includes a path planning unit (261) that plans a plurality of paths connecting a start point to an end point in a facility in which the irradiation system for particle therapy is provided, and a traffic management unit (262) that instructs the patient shuttle system to move on a path selected from a plurality of paths planned by the path planning unit.

[5] The irradiation system for particle therapy according to [4], wherein the transfer unit further has a sensor (136), wherein while moving on a path instructed by the navigation controller, the patient shuttle system acquires, from the sensor, information on a space including the path and transmits, to the navigation controller, position information on the patient shuttle system calculated by matching the information on the space with known map information, wherein while moving on the path, the patient shuttle system transmits a detection signal to the navigation controller in response to the sensor detecting an obstacle, and wherein the traffic management unit of the navigation controller instructs the patient shuttle system to move on another path selected from a plurality of paths planned by the path planning unit.

[6] The irradiation system for particle therapy according to [4] or [5], wherein the start point is a patient positioning room in the facility, and the end point is a treatment room for particle therapy in the facility, and wherein the patient shuttle system moves from the patient positioning room to the treatment room for particle therapy while maintaining the home position state.

[7] The irradiation system for particle therapy according to any one of [4] to [6], wherein the irradiation system for particle therapy further includes a patient positioning device (220) and a patient positioning device (230) provided in a patient positioning room and a treatment room for particle therapy of the facility, respectively, for positioning of an affected part of a patient relative to an isocenter of the particle beam, a patient positioning room management device (240) that manages the patient positioning device (220) in the patient positioning room and the patient shuttle system that entered the patient positioning room, and a treatment room management device (250) that manages the patient positioning device (230) in the treatment room for particle therapy and the patient shuttle system that entered the treatment room for particle therapy, wherein the patient positioning room management device and the treatment room management device share, via a network (270), patient positioning data generated by using the patient positioning device of the patient positioning room and the patient positioning device of the treatment room for particle therapy, wherein the patient shuttle system further comprises a base lock mechanism (137) that engages with lock receiving parts (225, 235) provided in the patient positioning room and the treatment room for particle therapy, respectively, to fix the patient shuttle system to the patient positioning room and the treatment room for particle therapy, wherein when the base lock mechanism engages with each of the lock receiving parts, the transfer unit enters a standby state, and the patient table drive unit recovers from a standby state, and wherein when the base lock mechanism releases engagement with each of the lock receiving parts, the transfer unit recovers from a standby state, and the patient table drive unit enters a standby state.

[8] The irradiation system for particle therapy according to [7], wherein during particle beam irradiation, in response to receiving an error signal from the patient table drive unit and/or the transfer unit, the treatment room management device transmits a signal to the particle beam irradiation apparatus to stop irradiation of a particle beam from the particle beam irradiation apparatus.

BRIEF DESCRIPTION OF THE DRAWINGS

FIGS. 2a to 2d illustrate diagrams illustrating motion and rotation of a patient table of the patient shuttle system.

DESCRIPTION OF THE EMBODIMENTS

Patient Shuttle System

Figure 1A:
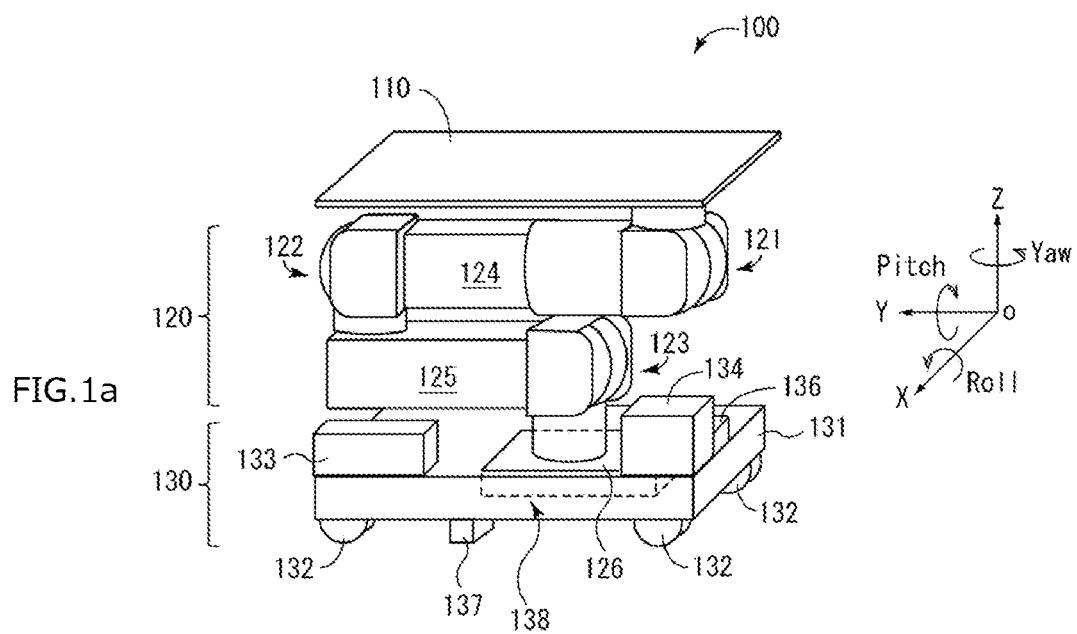
FIGS. 1a and 1b illustrate schematic diagrams of a configuration of a patient shuttle system according to one embodiment of the present invention.
Figure 1B:
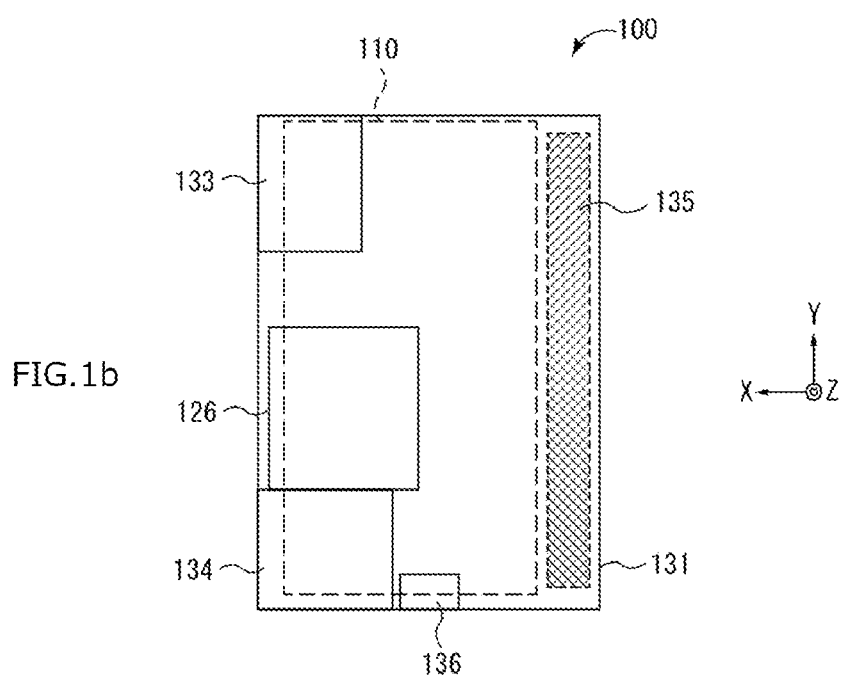

A patient shuttle system 100 according to one embodiment of the present invention will be described. FIG. 1a is a schematic diagram of a configuration of the patient shuttle system 100, and FIG. 1b is a plan view thereof.

In the present invention, the height direction of the patient shuttle system 100 is defined as a Z-axis, and axes orthogonal to each other in a plane perpendicular to the Z-axis are defined as an X-axis and a Y-axis. Rotation about the X-axis is defined as roll rotation, rotation about the Y-axis is defined as pitch rotation, and rotation about the Z-axis is yaw rotation. In the example of FIGS. 1a and 1b, a shorter-side direction of a patient table 110 that is rectangular in plan view is defined as the X-axis, the longer-side direction of the patient table 110 is defined as the Y-axis, and the height direction of the patient shuttle system 100 is defined as the Z-axis. Note that, when the patient table 110 is elliptical, the shorter axis may be the X-axis, the longer axis may be the Y-axis, and the axis perpendicular to both the axes may be the Z-axis.

The patient shuttle system 100 includes the patient table 110 that carries a patient, a patient table drive unit 120 that moves and rotates the patient table 110, and a transfer unit 130 that carries the patient table 110 and the patient table drive unit 120 thereon and moves.

The patient table 110 is not limited to be of a rectangular shape (a rectangle or a square) in plan view and may be of an elliptical shape (including a circle). The patient table 110 is stable (does not deflect) even when a patient is carried thereon and has a shape and a size such that a patient can be secured thereon so as not to move.

The patient table 110 has an immobilization device (not illustrated) for securing a patient body. The immobilization device may be a tool to secure a head of a patient, a tool to secure arms and legs of a patient, a tool to secure a trunk of a patient, and/or a cushioning material or the like formed along a shape of a patient body. Further, the patient table 110 may be configured such that a part of the patient table 110, such as a portion that comes into contact with a head, a leg, and/or a trunk of a patient may be inclined. Further, respiratory holes or the like may be provided in the patient table 110 so that a patient can be secured even when the patient lies face down on the patient table 110.

The patient table drive unit 120 includes a first rotating mechanism 121 connected to the patient table 110 and configured to rotate the patient table 110, a first arm 124 connected to the first rotating mechanism 121, a second rotating mechanism 122 connected to the first arm 124 and configured to rotate the first arm 124, a second arm 125 connected to the second rotating mechanism 122, and a third rotating mechanism 123 connected to the second arm 125 and configured to rotate the second arm 125.

The first to third rotating mechanisms 121 to 123 include drive motors (references 121a to 123a in FIG. 3) that move and rotate the patient table 110, the first arm 124, and the second arm 125 in response to receiving power from a battery (not illustrated) mounted on the patient shuttle system 100, encoders (references 121b to 123b in FIG. 3) that calculate moving amounts and rotating amounts (rotating direction) and output the calculated amounts to the drive control unit 133, and the like.

The first arm 124 is connected to the first and second rotating mechanisms 121 and 122, and the second arm 125 is connected to the second and third rotating mechanisms 122 and 123. The first and second arms 124 and 125 may be configured to expand and contract. In such a case, the first and second arms 124 and 125 have drive motors (references 124a and 125a in FIG. 3) that expand and contract the first and second arms 124 and 125 in response to receiving power from a battery (not illustrated) mounted on the patient shuttle system 100, encoders (references 124b and 125b in FIG. 3) that calculate amounts of expansion and contraction and output the calculated amounts to the drive control unit 133, and the like. The first and second arms 124 and 125 do not have these drive motors and encoders when not configured to expand or contract.

In one implementation, the first rotating mechanism 121 is configured to perform roll rotation, pitch rotation, and yaw rotation on the patient table 110. The second rotating mechanism 122 is configured to perform roll rotation and yaw rotation on the first arm 124. The third rotating mechanism 123 is configured to perform roll rotation and yaw rotation on the second arm 125. Further, the first and second arms 124 and 125 do not expand or contract.

The third rotating mechanism 123 is supported by a robot arm base 126, and the robot arm base 126 is fixed to a recess 138 provided in a base 131 of a transfer unit 130. The recess 138 is a portion recessed from the surface of the base 131 and preferably formed in a size such that the whole robot arm base 126 can be embedded in the base 131. As illustrated in FIG. 1b, the robot arm base 126 is arranged at a position off the center of the base 131 in plan view. Accordingly, the patient table 110, the first to third rotating mechanisms 121 to 123, the first and second arms 124 and 125, and the robot arm base 126 overlapped with each other in the height direction (Z-axis) are arranged at a position off the center in plan view, and a helper space 135 where a helper may ride on the base 131 is thus secured. When the base 131 is rectangular in plan view, the center of the base 131 is an intersection point of diagonal lines, and when the base 131 is circular (or elliptical in plan view), is the center of a circle (or an intersection point of the shorter axis and the longer axis). The helper space 135 can be any space as long as it has an area sufficient for at least one helper to stand (or sit down) therein and can be, for example, 0.1 m$^2$ or larger, 0.3 m$^2$ or larger, 0.5 m$^2$ or larger, 0.7 m$^2$ or larger, 1 m$^2$ or larger, 1.2 m$^2$ or larger, 1.5 m$^2$ or larger, or 2 m$^2$ or larger.

As illustrated in FIG. 1a, the patient table 110, the first to third rotating mechanisms 121 to 123, and the first and second arms 124 and 125 are configured to be able to be accommodated after folded so as to overlap each other in the height direction (Z-axis). This state is referred to as the patient shuttle system 100 being in a home position state. That is, when the patient shuttle system 100 is in the home position state, the patient table 110, the first arm 124, and the second arm 125 are in a state of being folded in the height direction (Z-axis).

In further description, when the patient shuttle system 100 is in the home position state, the first rotating mechanism 121 connected to one end of the patient table 110, the second rotating mechanism 122 arranged under the other end of the patient table 110, and the first arm 124 connected to the first and second rotating mechanisms 121 and 122 are configured to overlap the patient table 110 in the height direction (Z-axis). Further, when the patient shuttle system 100 is in the home position state, the second arm 125 and the third rotating mechanism 123 are configured to overlap the second rotating mechanism 122 and the first arm 124 (and the first rotating mechanism 121) in the height direction (Z-axis).

When the patient shuttle system 100 is in the home position state in such a way, the extent of the patient table 110 and the patient table drive unit 120 in the plane direction (XY plane) can be suppressed. The patient shuttle system 100 carries a patient on the patient table 110 while being in the home position state and moves in a facility such as a hospital.

The patient table drive unit 120 uses the first to third rotating mechanisms 121 to 123 to move and rotate the patient table 110 and the first and second arms 124 and 125 (and also to expand and contract the first and second arms 124 and 125 when configured to expand and contract) to move the patient table 110 to any position.

As illustrated in FIGS. 1a and 1b, the robot arm base 126 is installed so as to be embedded in the recess 138 of the base 131 and makes the height of the patient table in the home position as low as possible, the third rotating mechanism 123 maintains a space to the floor in the height direction, and thereby the second arm 125 can lower the patient table in the height direction. For example, as illustrated in FIG. 2a, the patient table drive unit 120 can lower the patient table 110 to come closer to the floor, and this makes it easier for a patient to get on and off the patient table 110. Further, as illustrated in FIG. 2b to FIG. 2d, the patient table drive unit 120 can move and rotate the patient table 110 during particle therapy to move the patient to any posture.

The rotating directions (roll rotation, pitch rotation, and/or yaw rotation) of the patient table 110, the first arm 124, and the second arm 125 and the amounts of rotation provided by the first to third rotating mechanisms 121 to 123 are suitably adjusted for specific implementation. When the first and second arms 124 and 125 are configured to expand and contract, the amounts of expansion and contraction of the first and second arms 124 and 125 are also suitably adjusted for specific implementation.

The transfer unit 130 includes the base 131, a plurality of (three or more) wheels 132 mounted to the base 131, a drive control unit 133 and a transfer control unit 134 placed on the base 131, one or a plurality of sensors 136 provided to the base 131, and a base lock mechanism 137 provided to the base 131. The sensor 136 has a spatial recognition sensor and an obstacle sensor. The spatial recognition sensor is a 2D, 3D laser range finder (3D laser range scanner (LiDAR)) or the like, for example, and recognizes the surrounding environment and generates three-dimensional point group data (spatial information), for example, in order to estimate the position of the patient shuttle system 100. The spatial information from the spatial recognition sensor is matched with known map information, thereby the position of the patient shuttle system 100 is estimated, and position information is generated. The sensor 136 is provided at a position (a front area, a rear area, one or more of four corners, or the like) where the sensor 136 is able to perform spatial recognition and detect an obstacle when the patient shuttle system 100 is moving, and the base lock mechanism 137 is provided on the side facing the floor or any one or more side faces of the front, rear, left, or right of the base 131. The patient shuttle system 100 acquires information on a space including a path by using the sensor 136 while moving on the path instructed by a navigation controller 260 described later, matches the information on the space with known map information prestored in the patient shuttle system 100, thereby calculates its position information (on the patient shuttle system 100), and transmits the calculated position information to the navigation controller. This enables the navigation controller 260 to recognize the position of the patient shuttle system 100.

The patient shuttle system 100 travels by itself in a facility by using a known technology. The patient shuttle system 100 is preferably of an autonomous mobile type having a self-positioning estimation function and a traveling control function but may be of a magnetic guide type, an electromagnet guide type, an image recognition scheme such as for a two-dimensional code, or a laser guide type. Further, the patient shuttle system 100 may be of a follow type that follows or moves in cooperation with a helper or the like or may be of a combination type that can switch the traveling mode in accordance with a situation.

The wheels 132 each are a drive wheel that can move in all the directions (omni-directional drive wheel) and preferably a mecanum wheel or an omni wheel. The wheel 132 is rotated in response to receiving force of a wheel drive motor (not illustrated) under the control of the transfer control unit 134 and causes the patient shuttle system 100 to travel. Although the patient shuttle system 100 travels by itself, a helper or the like may move the patient shuttle system 100 manually.

The patient shuttle system 100 may have an operation panel (not illustrated) or an emergency stop button as a safety function (not illustrated) so that a helper on the helper space 135 can manually drive the patient shuttle system 100 during traveling and may apply emergency stop of the patient shuttle system 100 in the event of emergency. The patient shuttle system 100 may be provided with a pendant (remote controller) that communicates with the drive control unit 133 in a wired or wireless manner so that, from the pendant, a helper or the like can instruct the patient table drive unit 120 to move. The patient shuttle system 100 may be configured such that a patient is allowed to get on or off the patient table 110 anywhere in a facility or get on or off the patient table 110 via the helper space 135 in the event of a sudden change in the patient's condition or the like, for example. Further, an obstruction guard (not illustrated) that repels small obstacles may be provided to the base 131 so that, for example, a small obstacle on the floor does not get caught in the wheel 132 when the patient shuttle system 100 is moving. Further, the patient shuttle system 100 may have a light emitting unit or a voice unit (both not illustrated) as a safety function during traveling. The light emitting unit is formed of an LED light or the like and displays the current status (traveling/standby/slowing down and stopping/abnormal state, or the like) of the patient shuttle system 100 by colors or manners of turning on and off of light so that the current status can be easily confirmed. Further, a winker function may be employed. The voice unit notifies persons therearound of a traveling direction or a direction indication by a melody or voice.

The drive control unit 133 is a computer having an interface such as an antenna to wirelessly communicate with a management device (a patient positioning room management device 240 and a treatment room management device 250 described later) for an irradiation system for particle therapy 200 described later, a program and a processor (or ASIC or the like) used for controlling the patient table drive unit 120 based on an instruction (control signal) from the management device described above, a memory used for storing the program or various information, and the like. The drive control unit 133 controls driving of the first to third rotating mechanisms 121 to 123 and the first and second arms 124 and 125 to control motion, rotation, and posture of the patient table 110 in accordance with an instruction received from the management device described above through wireless communication.

Figure 3:
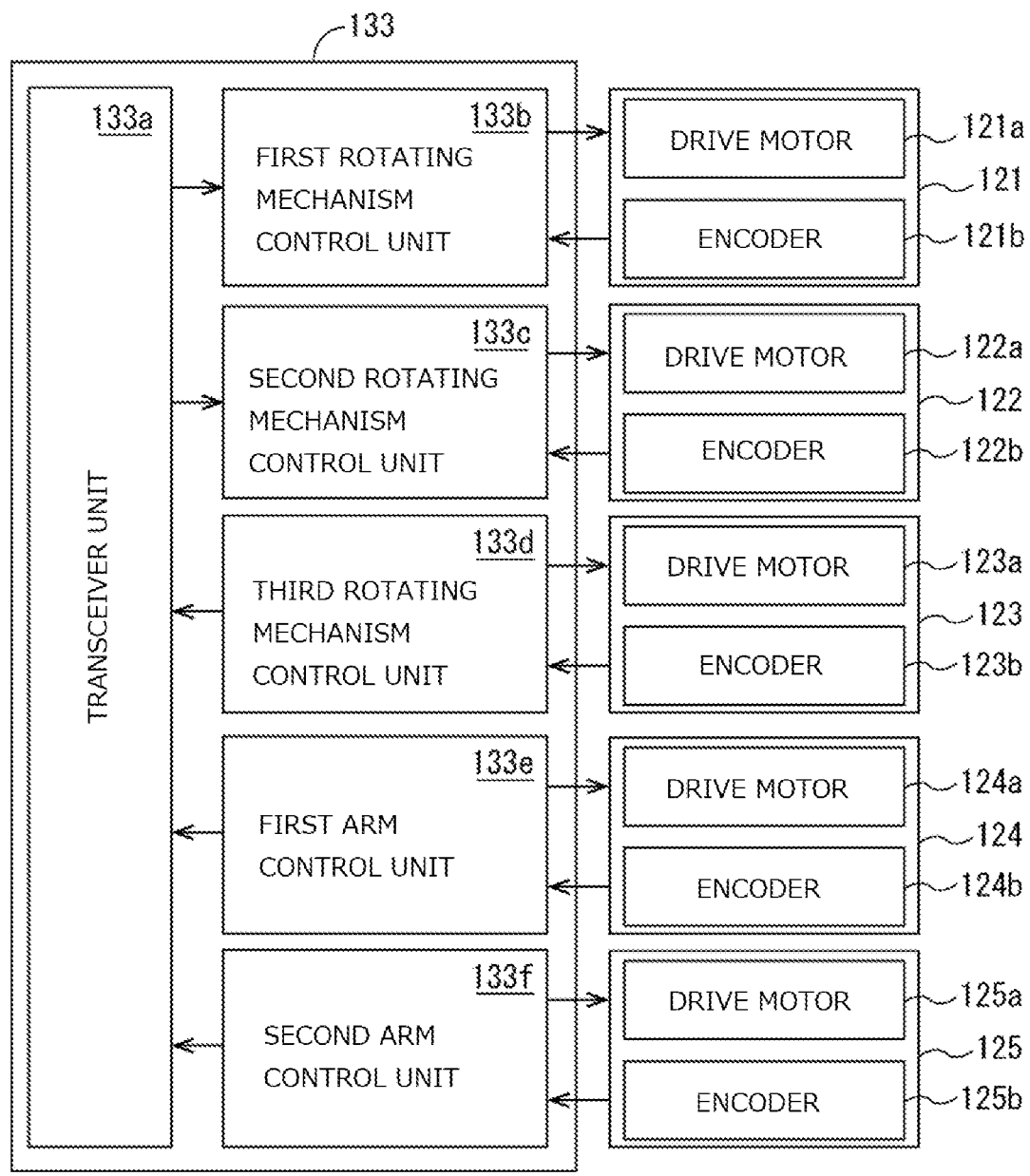
FIG. 3 is a block diagram of a drive control unit of the patient shuttle system.

FIG. 3 is a function block diagram of the drive control unit 133. The drive control unit 133 includes a transceiver unit 133a, which transmits and receives information to and from the management device described above, and a first rotating mechanism control unit 133b, a second rotating mechanism control unit 133c, and a third rotating mechanism control unit 133d, which control the first to third rotating mechanisms 121 to 123, respectively, as a function unit implemented by cooperation of the program stored in the memory and the processor or the like.

The first rotating mechanism control unit 133b controls the drive motor 121a of the first rotating mechanism 121 to control rotation (roll rotation, pitch rotation, and/or yaw rotation) of the patient table 110 based on an instruction received from the management device described above. A rotation amount (a rotation amount of roll rotation, a rotation amount of pitch rotation, and/or a rotation amount of yaw rotation) is calculated by the encoder 121b and output to the first rotating mechanism control unit 133b. The first rotating mechanism control unit 133b transmits information on the rotation amount to the management device described above via the transceiver unit 133a. Based on the information, the management device described above recognizes the rotation amount of the first rotating mechanism 121.

The second rotating mechanism control unit 133c controls the drive motor 122a of the second rotating mechanism 122 to control rotation (roll rotation, pitch rotation, and/or yaw rotation) of the first arm 124 based on an instruction received from the management device described above. A rotation amount (a rotation amount of roll rotation, a rotation amount of pitch rotation, and/or a rotation amount of yaw rotation) is calculated by the encoder 122b and output to the second rotating mechanism control unit 133c. The second rotating mechanism control unit 133c transmits information on the rotation amount to the management device described above via the transceiver unit 133a. Based on the information, the management device described above recognizes the rotation amount of the second rotating mechanism 122.

Similarly, the third rotating mechanism control unit 133d controls the drive motor 123a of the third rotating mechanism 123 to control rotation (roll rotation, pitch rotation, and/or yaw rotation) of the second arm 125 based on an instruction received from the management device described above. A rotation amount (a rotation amount of roll rotation, a rotation amount of pitch rotation, and/or a rotation amount of yaw rotation) is calculated by the encoder 123b and output to the third rotating mechanism control unit 133d. The third rotating mechanism control unit 133d transmits information on the rotation amount to the management device described above via the transceiver unit 133a. Based on the information, the management device described above recognizes the rotation amount of the third rotating mechanism 123.

When the first and second arms 124 and 125 are configured to be able to expand and contract, the drive control unit 133 further includes a first arm control unit 133e and a second arm control unit 133f. The first arm control unit 133e controls the drive motor 124a of the first arm 124 to control expansion and contraction of the first arm 124 based on an instruction received from the management device described above. The amount of expansion and contraction is calculated by the encoder 124b and output to the first arm control unit 133e. The first arm control unit 133e transmits information on the amount of expansion and contraction to the management device described above via the transceiver unit 133a. Based on the information, the management device described above recognizes the amount of expansion and contraction of the first arm 124. The same applies to the second arm control unit 133f, and the description thereof will be omitted.

The transfer control unit 134 is a computer having an interface such as an antenna to wirelessly communicate with a management device (the patient positioning room management device 240, the treatment room management device 250, and the navigation controller 260 described later) for the irradiation system for particle therapy 200 described later, a program and a processor (or ASIC or the like) used for controlling the transfer unit 130 based on an instruction from the management device described above, a memory used for storing the program or various information, and the like.

Figure 4:
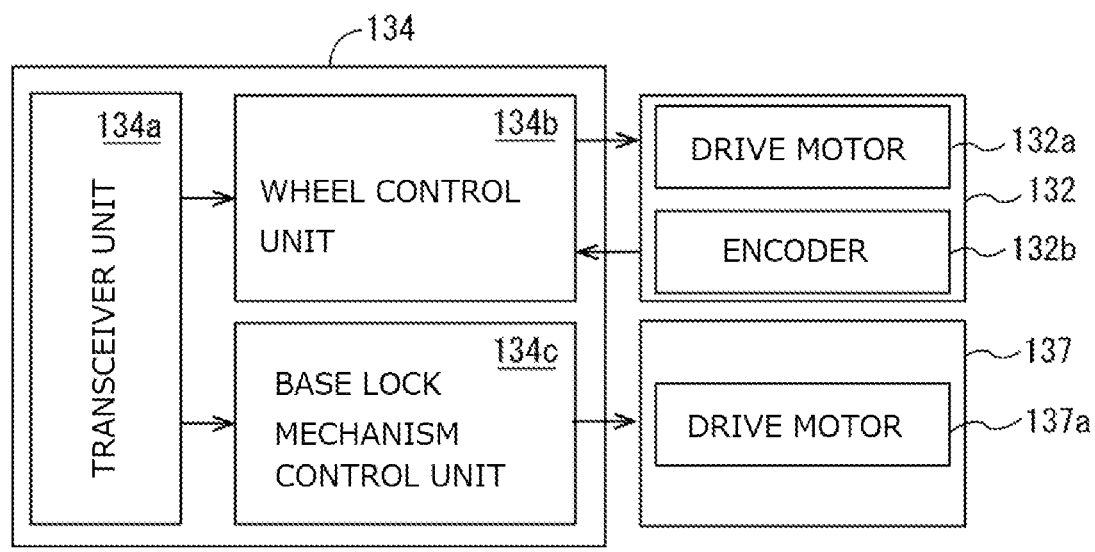
FIG. 4 is a block diagram of a transfer control unit of the patient shuttle system.

FIG. 4 is a function block diagram of the transfer control unit 134. The transfer control unit 134 includes a transceiver unit 134a that transmits and receives a signal to and from the management device described above, a wheel control unit 134b that controls the wheels 132, and a base lock mechanism control unit 134c that controls the base lock mechanism 137, as a function unit implemented by cooperation of the program stored in the memory and the processor or the like.

The wheel control unit 134b controls the drive motor 132a to control the rotation and the orientation of the wheel 132 based on an instruction received from the management device described above. In accordance with the instruction from the management device described above, the transfer control unit 134 controls the wheel 132, and the patient shuttle system 100 travels by itself in a facility. Rotation amounts (such as a speed and a traveling distance) of the wheel 132 are calculated by the encoder 132b and output to the wheel control unit 134b. The wheel control unit 134b transmits information on the rotation amounts to the management device described above via the transceiver unit 134a.

The base lock mechanism control unit 134c controls the drive motor 137a to control the base lock mechanism 137 into a locked state (to project from the base 131 and engage with a lock receiving part) or an unlocked state (to release engagement with the lock receiving part for storage in the base 131) based on an instruction received from the management device described above.

The obstacle sensor included in the sensor 136 is of a contactless type, which detects a nearby obstacle within a predetermined range from the patient shuttle system 100 (for example, several centimeters to several meters), and may be, for example, a two-dimensional or three-dimensional optical sensor, a laser measurement sensor, an acoustic sensor, a magnetic field sensor, an electric field sensor, an induction sensor, a radio wave sensor, or a combination thereof. Once detecting an obstacle, the sensor 136 transmits a detection signal to the transfer control unit 134 and a navigation controller described later, and in response thereto, the transfer control unit 134 and the navigation controller 260 control the patient shuttle system 100 to stop or avoid the obstacle. Note that a contact type sensor may be provided as a sensor that detects an obstacle. Such contact type sensor is provided around a portion where an expanded part may be the largest in the plane direction (XY plane), such as the base 131 or the patient table 110, and in response to the sensor coming into contact with an obstacle, the transfer control unit slows down and stops the patient shuttle system 100.

The base lock mechanism 137 is a mechanism that mechanically engages with a lock receiving part (225 in FIGS. 6a and 6b, 235 in FIG. 7) provided on the floor or a wall of a treatment room for particle therapy and a patient positioning room (locked state) and fixes the patient shuttle system 100 so as not to move with respect to the floor. The base lock mechanism 137 and the lock receiving part may be an air clamp using an air pressure or a mechanism using magnetic force for fixing instead of or in addition to a mechanism for mechanical engagement. Even when the patient shuttle system 100 is fixed in a room and the patient table drive unit is moved to an asymmetrical position with respect to the base 131 by using the base lock mechanism 137 and the lock receiving part provided on the floor, the wall, or the like of a treatment room for particle therapy and a patient positioning room, it is possible to maintain a desired lying position of a patient and hold the position stationary. Note that the mechanism to engage the base lock mechanism 137 and the lock receiving part to each other may be provided on the lock receiving part side instead of on the base lock mechanism 137 side.

The base lock mechanism 137 may be configured to be stored inside the base 131 so as not to be an obstacle during movement of the patient shuttle system 100 when not engaged with the lock receiving part (unlocked state) and to project from the base 131 and engage with the lock receiving part when engaged with the lock receiving part provided in a treatment room for particle therapy or the like. Note that, when the lock receiving part is provided on the wall face or the like of a treatment room for particle therapy or the like, the base lock mechanism 137 is also provided on the side or the like of the base 131 accordingly.

Note that, as a modified example of the base lock mechanism 137, the base lock mechanism may be stored in the wall or the floor of a treatment room for particle therapy or the like instead of being installed in the patient shuttle system 100. In such a case, the base lock mechanism may be configured to be stored in the wall or the floor of the treatment room for particle therapy or the like so as not to be an obstacle during movement of the patient shuttle system 100 when not engaged with the lock receiving part provided to the base 131 (unlocked state) and may be configured to project from the wall or the floor and engage with the lock receiving part when engaged with the lock receiving part. Further, an XYZ stage may be provided to the base lock mechanism to enable selection of a position for fixing. Accordingly, the position of engagement between the patient shuttle system 100 and the base lock mechanism can be a desired position without being fixed. Further, the distance between the patient shuttle system 100 and the base lock mechanism may be measured by a displacement sensor (not illustrated) installed to the base lock mechanism, and based on the proximity amount thereof, the transfer control unit 134 may operate the wheel 132 of the transfer unit 130 so as to be guided to a fixing position fixed to the lock receiving part. The displacement sensor is a sensor that detects force received when the patient shuttle system 100 comes into contact with the base lock mechanism installed at a fixed position or detects a change in a field or the like caused because the patient shuttle system 100 comes closer to the base lock mechanism installed at a fixed position, and the displacement sensor is a contact type sensor, an optical type sensor, an eddy current type sensor, or a combination thereof, for example.

A battery mounted on the patient shuttle system 100 may be charged through an auto-connector (not illustrated) provided to the base lock mechanism 137 or the like.

As described above, the patient shuttle system 100 according to the present embodiment is characterized in mainly including the following features. The patient shuttle system 100 includes the patient table 110 adapted to carry a patient, the patient table drive unit 120 that moves and rotates the patient table 110 to any position, and the transfer unit 130 that moves the patient shuttle system 100.

The patient table drive unit 120 moves and rotates the first and second arms 124 and 125 by using the first to third rotating mechanisms 121 to 123 (and when the first and second arms 124 and 125 are configured to expand and contract, also expands and contracts the same) to move the patient table 110 to any position. This enables the patient table drive unit 120 to move the patient table 110 closer to the floor, for example, and this makes it easier for a patient to get on and off the patient table 110.

When the patient shuttle system 100 is in the home position state, the first to third rotating mechanisms 121 to 123 and the first and second arms 124 and 125 are configured to overlap the patient table 110 in the height direction (Z-axis) such that the patient table 110, the first arm 124, and the second arm 125 are in a state of being folded in the height direction (Z-axis). Accordingly, it is possible to suppress the patient table 110 and the patient table drive unit 120 from extending in the plane direction (XY plane), and the patient table 110 and the patient table drive unit 120 are less likely to be an obstacle when the patient shuttle system 100 is moving. Further, since the robot arm base 126 is installed so as to be embedded in the recess 138 of the base 131, the height of the patient table at the home position can be as low as possible, the patient table 110 can be lowered to the floor as close as possible when a patient is getting on and off the patient table 110, and this makes it easier for the patient to get on and off the patient table 110.

Further, the robot arm base 126 that supports the third rotating mechanism 123 is fixed at a position off the center of the base 131 in plan view, and accordingly, the helper space 135 on which a helper can ride is secured on the base 131.

Irradiation System for Particle Therapy

The irradiation system for particle therapy 200 using the patient shuttle system 100 according to the present embodiment will be described. The irradiation system for particle therapy 200 includes one or a plurality of patient shuttle systems 100 and a particle beam irradiation apparatus 210, patient positioning devices 220 and 230, the patient positioning room management device 240, the treatment room management device 250, and the navigation controller 260.

Figure 5:
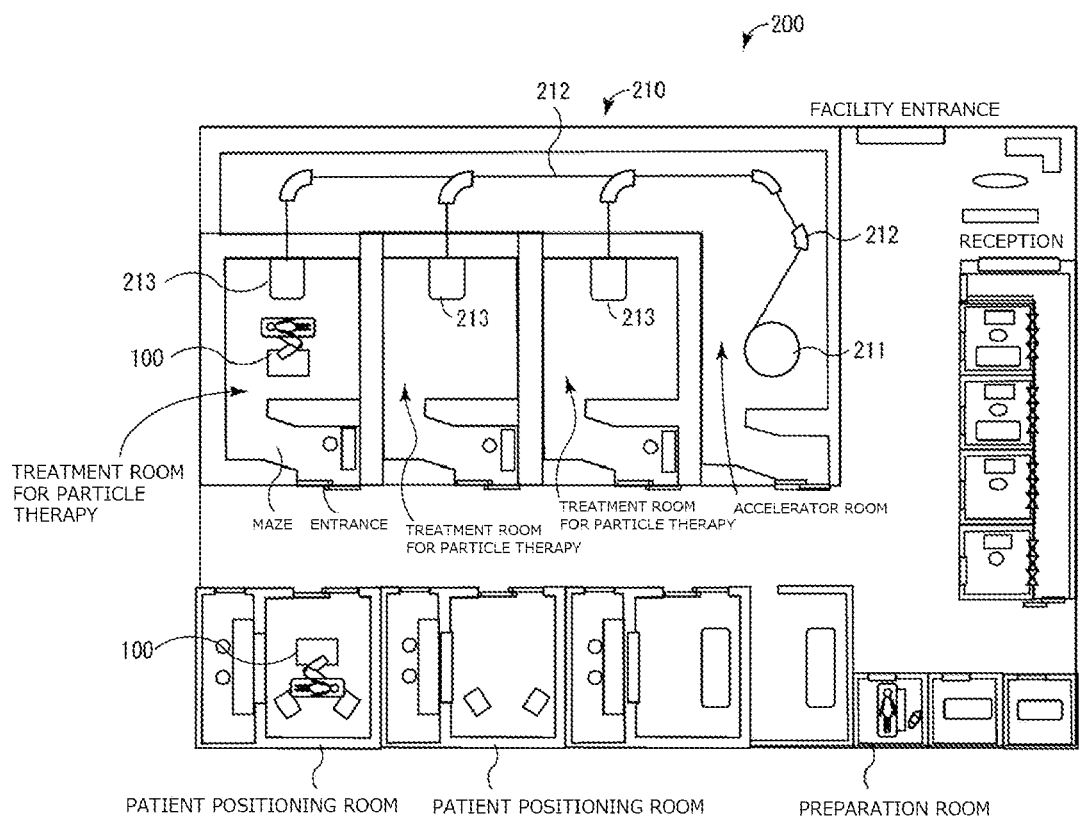
FIG. 5 is a schematic diagram of an irradiation system for particle therapy in a facility.

FIG. 5 illustrates an example of the irradiation system for particle therapy 200 provided in a facility (for example, a hospital) in which particle therapy is performed. The facility in which particle therapy is performed includes at least: one or a plurality of treatment rooms for particle therapy in which the particle beam irradiation apparatus 210 that irradiates a patient with a particle beam is arranged; and one or a plurality of patient positioning rooms in which a patient positioning process to match the position of an affected part of a patient to an irradiation position (isocenter IC) of the particle beam irradiation apparatus 210 is performed.

The particle beam irradiation apparatus 210 includes an accelerator 211 that generates a particle beam, a particle beam guide 212 including a vacuum duct through which a particle beam passes inside and various electromagnet units which adjust the direction, the intensity, the size, and the like of the particle beam, an irradiation nozzle 213 that irradiates a particle beam to an irradiation-target site of a patient, and an irradiation control unit 214 that controls the overall particle beam irradiation apparatus 210.

The accelerator 211 is a device that generates a particle beam, which is a proton beam, a neutron beam, or a heavy-ion beam, and is a synchrotron, a cyclotron, a synchrocyclotron, or a linear accelerator, for example. A particle beam generated by the accelerator 211 is guided to the irradiation nozzle 213 by the particle beam guide 212. The various electromagnet units of the particle beam guide 212 include a quadrupole magnet unit, a steering magnet unit, a bending magnet unit, a focusing magnet unit, a superconducting magnet unit, and/or the like disclosed in Japanese Patent No. 6364141, Japanese Patent No. 6387476, and Japanese Patent No. 6734610. Further, the various electromagnet units of the particle beam guide 212 may further include a beam slit unit that adjusts the shape and/or dose of a particle beam or a steering magnet unit that finely tunes a beam position of a particle beam. The contents disclosed in Japanese Patent No. 6364141, Japanese Patent No. 6387476, and Japanese Patent No. 6734610 are incorporated in the present invention by reference.

Figure 7:
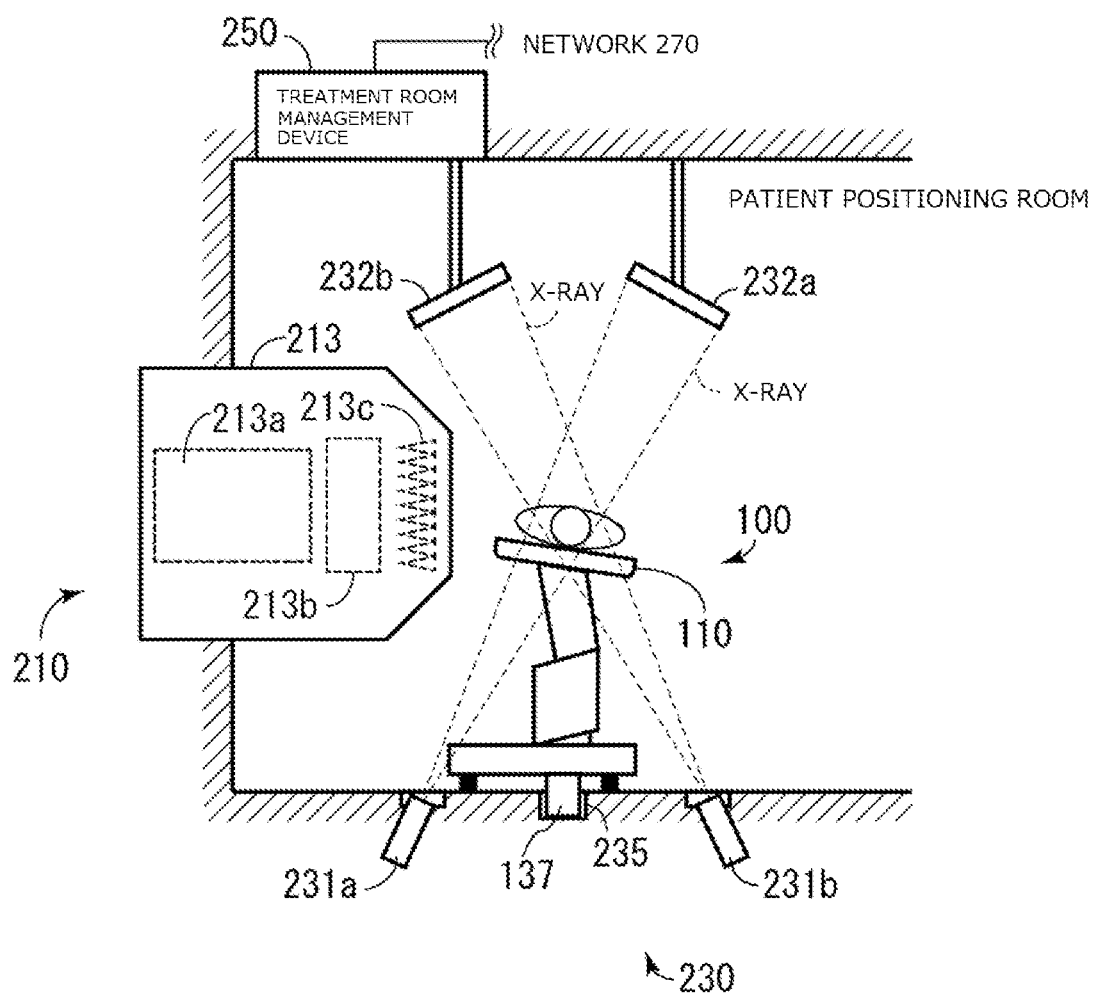
FIG. 7 is a schematic diagram of a treatment room for particle therapy in the irradiation system for particle therapy.

The irradiation nozzle 213 is provided inside a treatment room for particle therapy and irradiates a particle beam from the particle beam guide 212 to an affected part. The irradiation nozzle 213 has a scanning magnet 213a, a beam monitor 213b, and an energy modulation unit 213c (FIG. 7). The irradiation nozzle 213 is, for example, the irradiation nozzle disclosed in Japanese Patent No. 6387476.

The scanning magnet 213a is an electromagnet used for adjusting the flowing current amount or the current direction to adjust the traveling direction of a particle beam irradiated from the irradiation nozzle 213 and enable a scan within a predetermined range. The beam monitor 213b is a monitor that monitors a particle beam and measures the dose or the position and flatness of the beam. The measured information is fed back from the beam monitor 213b to the irradiation control unit 214 of the particle beam irradiation apparatus 210 and utilized for control of the scanning magnet 213a or for accurate irradiation of a particle beam. The energy modulation unit 213c adjusts the energy of a particle beam to adjust the depth inside a patient that the particle beam reaches and is a range modulator, a scatterer, a ridge filter, a patient collimator, a patient bolus, an applicator, or the like, for example.

The irradiation control unit 214 is a computer that communicates with the treatment room management device 250 of the treatment room for particle therapy, receives an instruction for the particle beam irradiation apparatus 210 from the treatment room management device 250, and based on the instruction, controls the accelerator 211, the particle beam guide 212, and the irradiation nozzle 213 of the particle beam irradiation apparatus 210.

In each patient positioning room, the patient positioning device 220 and the lock receiving part 225 configured to engage with the base lock mechanism 137 of the patient shuttle system 100 are installed (FIG. 6). The patient shuttle system 100 on which a patient is placed is transferred to a patient positioning room through inside of the facility, fixed by engagement of the base lock mechanism 137 to the lock receiving part 225 provided in the patient positioning room, and then directly used as a positioning table for patient positioning. It is not required to transfer a patient from a carriage, which is used for transferring a patient, to a positioning table, which is used for patient positioning, and this reduces the burden on the patient. Further, it is not required to install a fixed positioning table in a patient positioning room, and this contributes to a reduction in the space of the patient positioning room.

Although the lock receiving part 225 is formed on the floor in the configuration of FIG. 6, when the base lock mechanism 137 is provided to another portion such as a side face (or another part) of the base 131, the lock receiving part 225 is installed at a position corresponding thereto. Further, when a plurality of base lock mechanisms 137 are provided in the patient shuttle system 100, the corresponding number of lock receiving parts 225 are installed in a patient positioning room.

The patient positioning device 220 has a plurality of X-ray tubes 221 (221a, 221b in FIGS. 6a and 6b) and a plurality of detectors 222 (222a, 222b in FIGS. 6a and 6b) that detects an X-ray, such as a CCD area image sensor, a CMOS area image sensor, or a flat panel detector. The patient positioning device 220 is an X-ray image acquiring device or an X-ray CT device, for example. An MRI device may be used as the patient positioning device 220, and in such a case, a magnetic field generator (such as an electromagnet) will be used instead of the X-ray tube 221, and a magnetic field detector (such as an RF receiving coil) will be used as the detector 222.

Figure 6A:
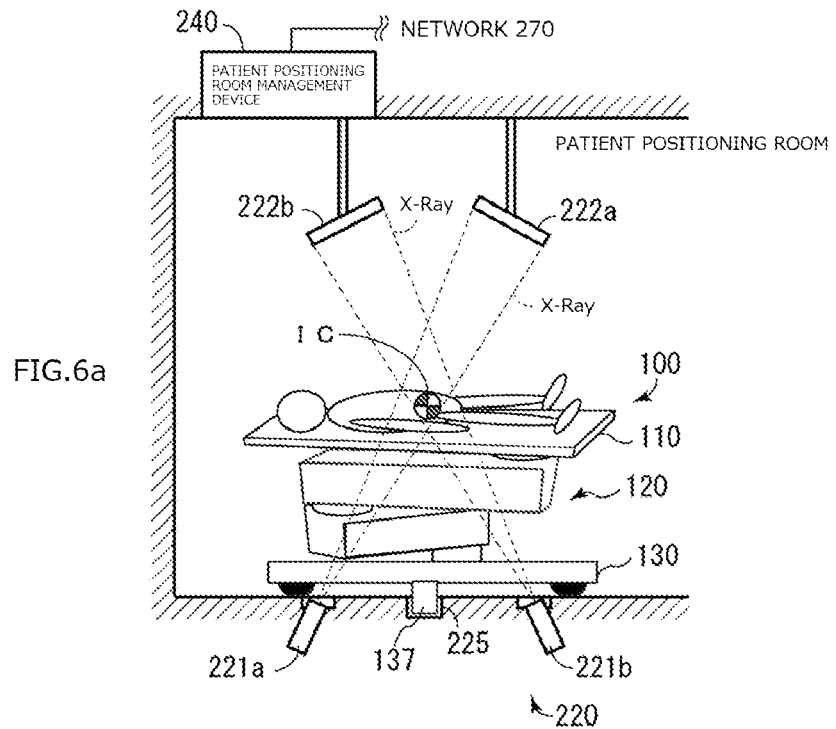
FIGS. 6a and 6b illustrate schematic diagrams of a patient positioning room in the irradiation system for particle therapy.
Figure 6B:
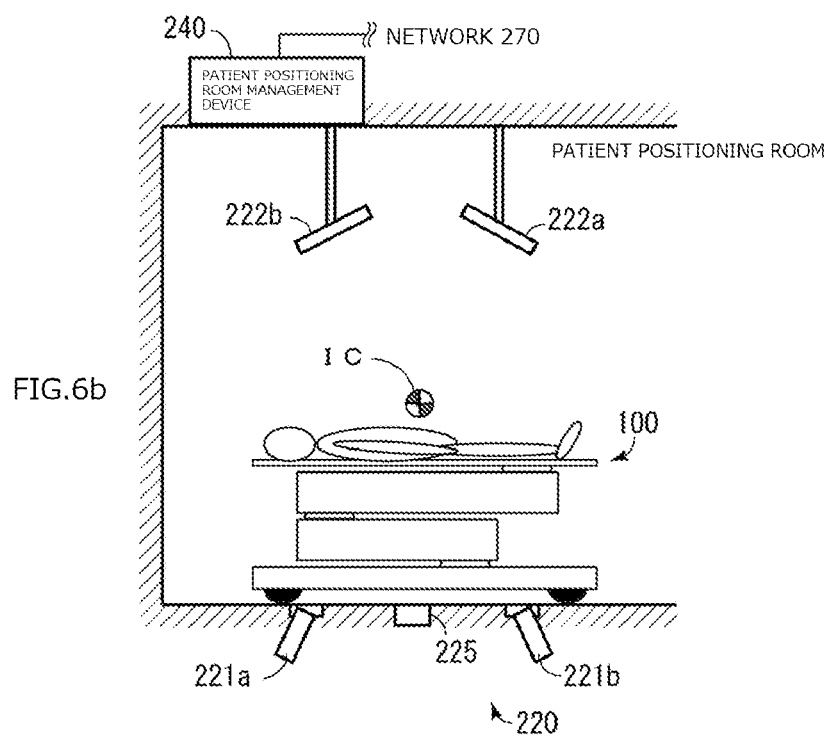

Although FIGS. 6a and 6b depicts two pairs of the X-ray tubes 221a, 221b and the corresponding detectors 222a, 222b, the number of these pairs may be one or may be three or greater. Since a larger number thereof improves accuracy but makes the process complex, the number of pairs is preferably two to four.

In the patient positioning room, positioning of an affected part relative to the position of the particle beam irradiation position (isocenter IC) is performed by using the patient positioning device 220 (FIG. 6a). The isocenter coordinate data (XYZ coordinates) and X-ray image data and further positioning data on the first to third rotating mechanisms 121 to 123 and the first and second arms 124 and 125 of the patient table drive unit 120 (that is, various data used for reproducing, in a treatment room for particle therapy, the three-dimensional positions and posture of the patient table 110 and the patient table drive unit 120 that have been taken in patient positioning) are transmitted to the patient positioning room management device 240 and then transmitted from the patient positioning room management device 240 to the treatment room management device 250 via a network 270. After completion of positioning of the particle beam irradiation position in the patient positioning room, the patient shuttle system 100 returns to the home position state while carrying a patient on the patient table 110 (FIG. 6b) and directly moves to a treatment room for particle therapy.

Each treatment room for particle therapy is surrounded by a shield of thick concrete or the like in order to prevent leakage of unnecessary radiation to the outside (FIG. 5). The entrance of the treatment room for particle therapy has maze structure having a crank, and this serves as a countermeasure against particle beam leakage.

In each treatment room for particle therapy, the particle beam irradiation apparatus 210 (in particular, the irradiation nozzle 213), the patient positioning device 230 that performs positioning of the particle beam irradiation position, and a lock receiving part 235 that engages with the base lock mechanism 137 of the patient shuttle system 100 are installed (FIG. 7). The patient shuttle system 100 on which a patient is placed is transferred into a treatment room for particle therapy through inside of the facility, fixed by engagement of the base lock mechanism 137 to the lock receiving part 235 provided in the treatment room for particle therapy, and then directly used as a table for particle therapy. It is not required to transfer a patient from a carriage, which is used for transferring a patient, to a table, which is used for treatment, and this reduces the burden on the patient. Further, it is not required to install a fixed treatment table in a treatment room for particle therapy, and the space of the treatment room for particle therapy can thus be reduced.

Although the lock receiving part 235 is formed on the floor in FIG. 7, when the base lock mechanism 137 is provided to a side face (or another part) of the base 131, the lock receiving part 235 is arranged at a position corresponding thereto. Further, when a plurality of base lock mechanisms 137 are provided, the corresponding number of lock receiving parts 235 are installed in a treatment room for particle therapy.

In the treatment room for particle therapy, a positioning process of an affected part relative to the particle beam irradiation position is again performed based on the patient positioning data received from the patient positioning room management device 240. Note that, although the patient positioning device 230 installed in a treatment room for particle therapy may have a different configuration from the patient positioning device 220 installed in a patient positioning room, it is preferable that both the patient positioning devices have the same configuration, because matching between patient positioning in a treatment room for particle therapy and patient positioning in a patient positioning room is facilitated.

The patient positioning device 220 in a patient positioning room may be provided such that a part thereof is provided inside the patient positioning room and the remaining part is provided outside the patient positioning room. Similarly, the patient positioning device 230 in a treatment room for particle therapy may be provided such that a part thereof is provided inside the treatment room for particle therapy and the remaining part is provided outside the treatment room for particle therapy. Thus, if a part of the patient positioning device 220 or 230 is provided inside a patient positioning room or a treatment room for particle therapy, this means "a patient positioning device provided in a patient positioning room" and "a patient positioning device provided in a treatment room for particle therapy".

The patient positioning device 220 has various communication interfaces, a program and a processor (or ASIC or the like) used for various control, a memory used for calculation of a displacement or importing of an acquired image during a patient positioning process, and the like. The patient positioning device 220 includes an X-ray image acquisition and processing control unit (not illustrated) as a function unit of the patient positioning device 220 implemented by cooperation of the program stored in the memory and the processor or the like.

The X-ray image acquisition and processing control unit controls the X-ray tube 221 and the detector 222 to generate an X-ray image of an affected part of a patient and output the X-ray image to a patient positioning unit in response to an instruction from the patient positioning room management device 240 or at a predetermined cycle. The patient positioning unit compares the input X-ray image with a prestored reference X-ray image related to the affected part of the patient, calculates an error amount (position error) between both the X-ray images, and outputs the information thereon to the patient positioning room management device 240. Further, a proximity amount between the base lock mechanism and the base 131 (that is, the patient shuttle system 100) detected by a displacement sensor provided in the base lock mechanism 137 may be transmitted to the patient positioning room management device 240 as a correction amount relative to a fixed position of the patient shuttle system 100, and the position error may be updated by adding a correction amount to the position error.

The patient positioning room management device 240 calculates moving amounts and/or rotating amounts of the patient table 110 and the patient table drive unit 120 of the patient shuttle system 100 so that the position error described above is reduced (or becomes zero) and transmits the information thereon to the drive control unit 133 of the patient shuttle system 100. In response thereto, the drive control unit 133 moves the patient table drive unit 120 to adjust the position of the patient table 110. Further, the patient positioning room management device 240 receives information on the actually applied moving amounts and/or rotating amounts from the patient shuttle system 100.

The patient positioning room management device 240 transmits various information to the treatment room management device 250 via the network 270. The various information includes information on moving amounts and/or rotating amounts received from the drive control unit 133 by the patient positioning room management device 240. Further, if there is a failure or the like in the patient shuttle system 100 or the base lock mechanism 137, an error signal is transmitted from the patient shuttle system 100 to the patient positioning room management device 240. The patient positioning room management device 240 that has received the error signal performs an operation of causing a warning to be displayed on a display screen or the like of the patient positioning device 220 to suggest retry of a patient positioning process, indicating error display to the operator to urge the operator to ensure safety of a patient, or the like.

The same as the patient positioning device 220 and the patient positioning room management device 240 in a patient positioning room applies for the patient positioning device 230 and the treatment room management device 250 in a treatment room for particle therapy, and the description thereof will be omitted. In particular, if an error signal due to motion, malfunction, or the like is received from the patient table drive unit 120 and/or the transfer unit 130 of the patient shuttle system 100 during particle therapy (irradiation), the treatment room management device 250 transmits a signal to the particle beam irradiation apparatus 210 to take an emergency action to stop the irradiation of a particle beam from the particle beam irradiation apparatus 210.

Figure 8:
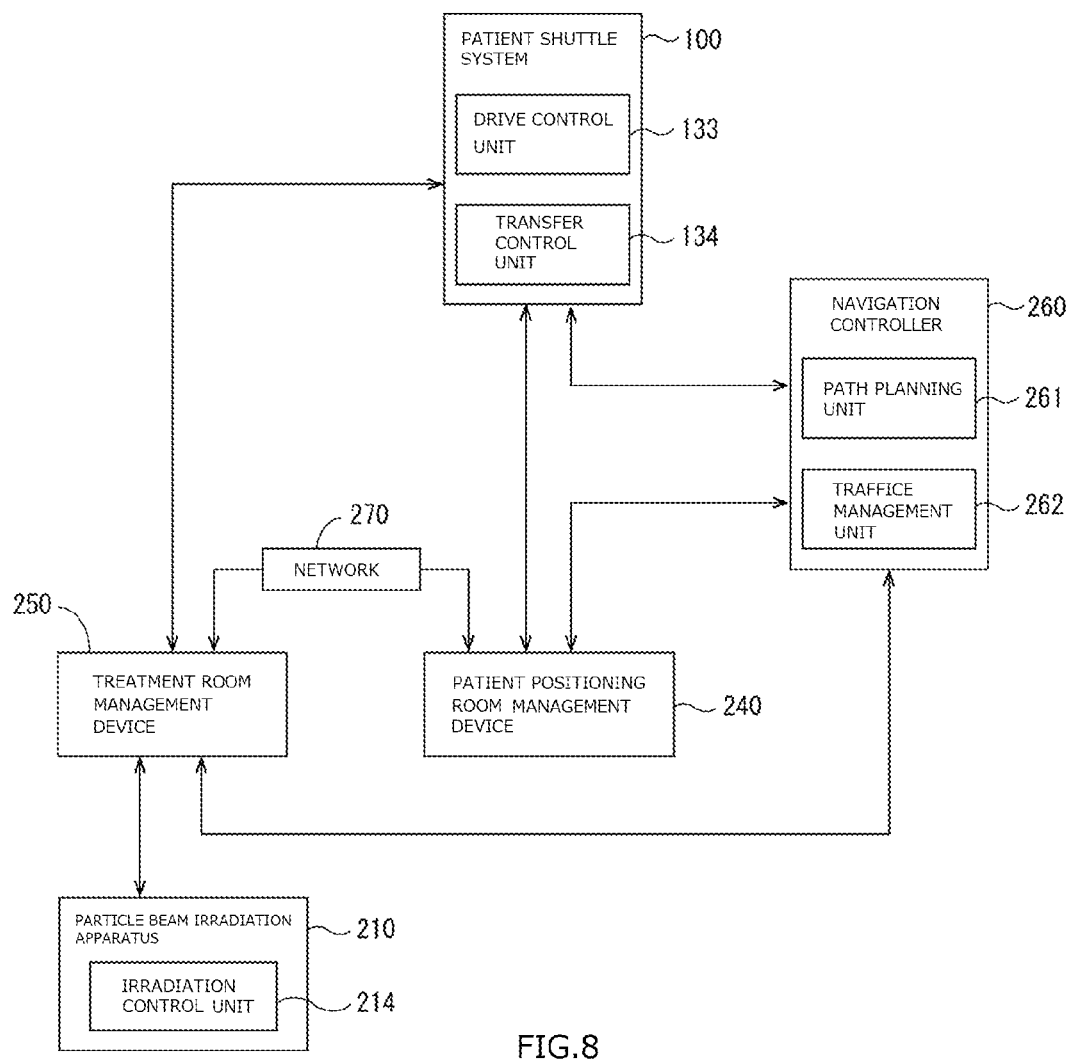
FIG. 8 is a control block diagram of the irradiation system for particle therapy.

The navigation controller 260 is a computer that manages traveling of the patient shuttle system 100. The navigation controller 260 communicates with the drive control unit 133 and the transfer control unit 134 of the patient shuttle system 100 to control these units and transfer various information. Further, the navigation controller 260 communicates with the patient positioning room management device 240 and the treatment room management device 250 and transfers various information (FIG. 8).

The navigation controller 260 is a computer having an interface, a program and a processor (or ASIC or the like) used for controlling the overall irradiation system for particle therapy 200, and a memory used for storing a program or various information or the like. The navigation controller 260 has a path planning unit 261 and a traffic management unit 262 that controls motion of the patient shuttle system 100 as a function unit implemented by cooperation of the program stored in the memory and the processor or the like.

To increase efficiency of particle therapy, it is required to shorten a treatment room occupancy time per a patient or, immediately after completion of particle therapy of a patient, guide a next patient to enter the treatment room for particle therapy. There may be a plurality of patient shuttle systems operated in treatment rooms for particle therapy or a facility outside treatment rooms for particle therapy, and a management device that knows the status of each patient shuttle system is required for operation of the plurality of patient shuttle systems. In view of such circumstances, the navigation controller 260 manages motion of the patient shuttle systems 100 inside a facility.

The path planning unit 261 has a function of generating and storing a map inside a facility for particle therapy. When one or a plurality of treatment rooms for particle therapy and one or a plurality of patient positioning rooms inside a facility for particle therapy are defined as start points and end points, respectively, the path planning unit 261 plans a plurality of paths connecting the start points to the end points. Herein, in general, in the facility for particle therapy, there may be a plurality of paths in a facility for particle therapy even between the same start point and the same end point for preventing patients from coming across each other or ensuring a traffic line for medical workers.

The path planning unit 261 maps in advance the structure inside the facility by using a known technology before performing path planning between start points and end points. The path planning unit 261 preferably uses a natural feature navigation (NFN) scheme to perform mapping. A plurality of paths planned by the path planning unit 261 are shared with the traffic management unit 262.

The traffic management unit 262 selects an optimal path from a plurality of motion paths planned by the path planning unit 261 and instructs the transfer control unit 134 of the patient shuttle system 100 to move along the selected path. The transfer control unit 134 operates the transfer unit 130 in accordance with an instruction from the traffic management unit 262 and causes the patient shuttle system 100 to move along the selected path.

When a plurality of patient shuttle systems 100 travels within a facility, there may be a congestion on a path. It is assumed that a first patient shuttle system 100 moves from a treatment room for particle therapy A as a start point and another second patient shuttle system 100 moves to the treatment room for particle therapy A as an end point. Before the first patient shuttle system 100 moving from the treatment room A exits the treatment room A, the second patient shuttle system 100 has to stand by, and this results in a reduction in the treatment efficiency of the overall facility. Thus, the traffic management unit 262 acquires position information on each patient shuttle system 100 at a constant cycle (for example, a cycle of 1 second) and selects the optimal path at each time.

Figure 9:
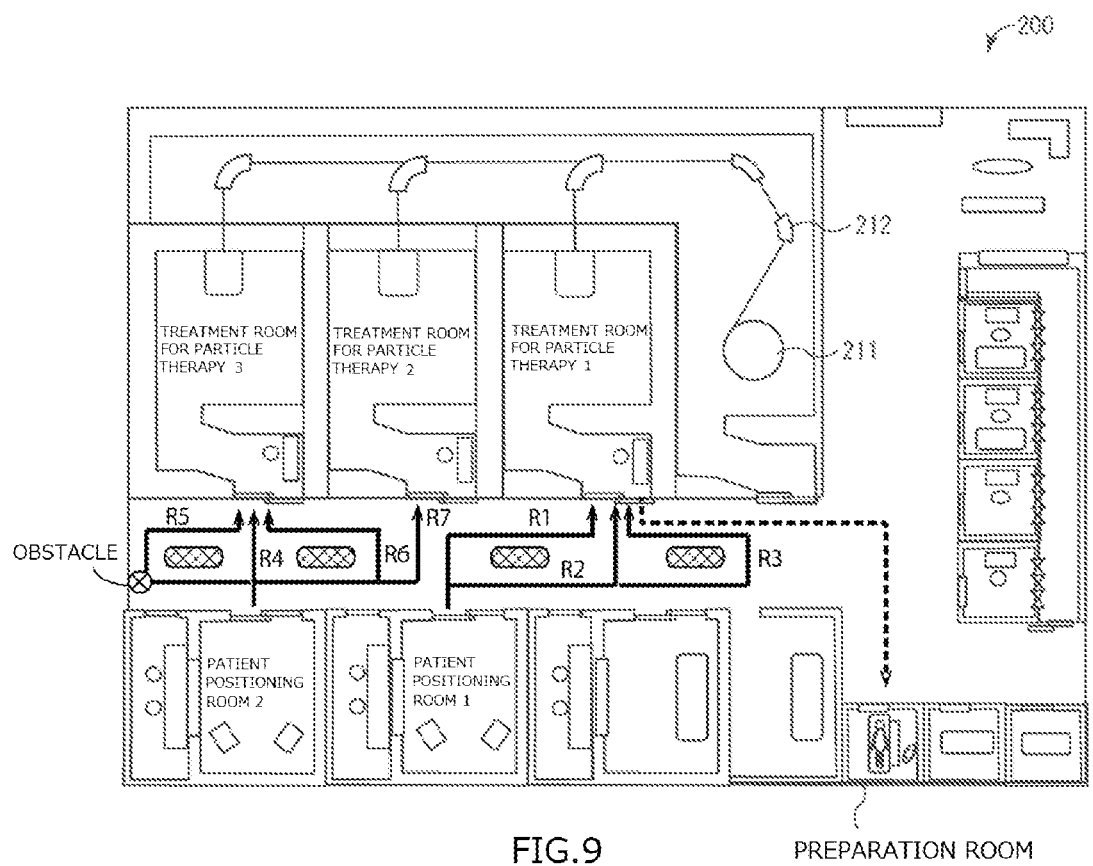
FIG. 9 is a diagram illustrating paths of the patient shuttle system.

For example, FIG. 9 illustrates that there are three paths R1 to R3 from a patient positioning room 1 (start point) to a treatment room for particle therapy 1 (end point) planned by the path planning unit 261 and there are three paths R4 to R6 from a patient positioning room 2 (start point) to a treatment room for particle therapy 3 (end point).

For example, when a patient shuttle system 100 moves to the treatment room for particle therapy 1 after completion of patient positioning in the patient positioning room 1, the patient shuttle system 100 moves along any one of the paths R1 to R3. At this time, when determining that another patient shuttle system 100 returning from the treatment room for particle therapy 1 to a preparation room is present (dashed line in FIG. 9), the traffic management unit 262 specifies the path of the patient shuttle system 100 exiting the patient positioning room 1 to the path R1 or R2 in order to avoid collision or congestion between both the patient shuttle systems and transmits such an instruction.

For example, when a patient shuttle system 100 moves to the treatment room for particle therapy 3 after completion of patient positioning in the patient positioning room 2, the patient shuttle system 100 moves along any one of the paths R4 to R6. At this time, when determining that another patient shuttle system 100 returning from the treatment room for particle therapy 3 to a preparation room slightly delays, the traffic management unit 262 specifies the path R5, which is a longer path, instead of the path R4, which is the shortest path as a path of the patient shuttle system 100 exiting the patient positioning room 2 in order to avoid collision or congestion between both the patient shuttle systems. Further, if the sensor 136 of the patient shuttle system 100 detects an unexpected obstacle while the patient shuttle system 100 is moving on the path R5, a detection signal is transmitted to the navigation controller 260. If the traffic management unit 262 receives the signal and determines that traffic is unavailable on the path R5, the traffic management unit 262 transmits an instruction to the patient shuttle system 100 to switch the path from the path R5 to the path R6 or R4 while taking the position of another moving patient shuttle system 100 into consideration.

For example, when a patient shuttle system 100 moves to the treatment room for particle therapy 3 after completion of patient positioning in the patient positioning room 2, it is assumed that the navigation controller 260 has not received an instruction from a treatment room management device in the treatment room for particle therapy 3 for recovering the transfer control unit 134 of another patient shuttle system 100 from a standby state. At this time, the navigation controller 260 determines that treatment is not completed in the treatment room 3, then communicates with a schedule management device (not illustrated) for radiation therapy to allocate the patient to any of vacant treatment rooms, and thereby regenerates a treatment schedule. For example, it is assumed that the patient is allocated to the treatment room 2, the navigation controller 260 specifies the path R7 as the path of the patient shuttle system 100 exiting the patient positioning room 2 and transmits such an instruction. The schedule management device for radiation therapy is the device disclosed in Japanese Patent No. 6632015, for example.

When an obstacle unknown at the path planning unit 261 is detected by the sensor 136 provided to the patient shuttle system 100, the patient shuttle system 100 is controlled to take an action to avoid the obstacle (including stop of traveling). Such an obstacle unknown at the path planning unit 261 may be, for example, a medical worker or a patient walking on the passage, luggage temporarily left on the passage, or the like. Once the obstacle is detected by the sensor 136, a detection signal is transmitted to the traffic management unit 262, and in accordance with an instruction from the traffic management unit 262, the transfer control unit 134 operates the wheels 132 of the transfer unit 130 so as to avoid the obstacle. Also for a case where the patient shuttle systems 100 pass each other, respective sensors 136 detect each other as an obstacle, and detection signals are transmitted to the traffic management unit 262 in the same manner as above. The traffic management unit 262 instructs respective transfer control units 134 how to avoid the patient shuttle systems 100, respectively, so that respective traveling is not prevented.

Next, switching of control of the patient shuttle system 100 when the patient shuttle system 100 has entered a patient positioning room and a treatment room for particle therapy will be described.

In response to completion of engagement between the base lock mechanism 137 and the lock receiving part 225 after the patient shuttle system 100 entered a patient positioning room (locked state), a signal indicating the establishment of the locked state is transmitted to the patient positioning room management device 240. In response thereto, the patient positioning room management device 240 transmits an instruction for controlling the transfer control unit 134 into a standby state and an instruction for recovering the drive control unit 133 from the standby state in order to prevent the patient shuttle system 100 from moving unexpectedly.

After completion of patient positioning, the patient positioning room management device 240 transmits a signal indicating the completion of patient positioning to the drive control unit 133, and in response thereto, the drive control unit 133 returns the patient table 110 to the home position state. After returning to the home position state, the drive control unit 133 transmits a signal indicating the recovery to the home position state to the patient positioning room management device 240. In response thereto, the patient positioning room management device 240 transmits an instruction to the transfer control unit 134, the transfer control unit 134 recovers from the standby state in response to receiving the instruction from the patient positioning room management device 240, and the drive control unit 133 enters a standby state. The transfer control unit 134 then controls the base lock mechanism 137 into the unlocked state and transmits a signal indicating the establishment of the unlocked state to the patient positioning room management device 240. In response thereto, the patient positioning room management device 240 transmits an instruction for permitting the patient shuttle system 100 to move (including specifying a path) to the transfer control unit 134. In response thereto, the transfer control unit 134 causes the patient shuttle system 100 to start moving, exit the patient positioning room, and move to a treatment room for particle therapy.

Similarly, in response to completion of engagement between the base lock mechanism 137 and the lock receiving part 235 after the patient shuttle system 100 entered a treatment room for particle therapy, a signal indicating the establishment of the locked state is transmitted to the treatment room management device 250. In response thereto, the treatment room management device 250 transmits an instruction for controlling the transfer control unit 134 into a standby state and an instruction for recovering the drive control unit 133 from the standby state in order to prevent the patient shuttle system 100 from moving unexpectedly.

After completion of particle therapy, the treatment room management device 250 transmits a signal for recovery to the home position of the drive unit 120 to the drive control unit 133, and in response thereto, the drive control unit 133 returns the patient table 110 to the home position state. After returning to the home position state, the drive control unit 133 transmits a signal indicating the recovery to the home position state to the treatment room management device 250. In response thereto, the treatment room management device 250 transmits an instruction to the transfer control unit 134, the transfer control unit 134 recovers from the standby state in response to receiving the instruction from the treatment room management device 250, and the drive control unit 133 enters a standby state. The transfer control unit 134 then controls the base lock mechanism 137 into the unlocked state and transmits a signal indicating the establishment of the unlocked state to the treatment room management device 250. In response thereto, the treatment room management device 250 transmits an instruction for permitting the patient shuttle system 100 to move (including specifying a path) to the transfer control unit 134. In response thereto, the transfer control unit 134 causes the patient shuttle system 100 to start moving and exit the treatment room for particle therapy.

Figure 10:
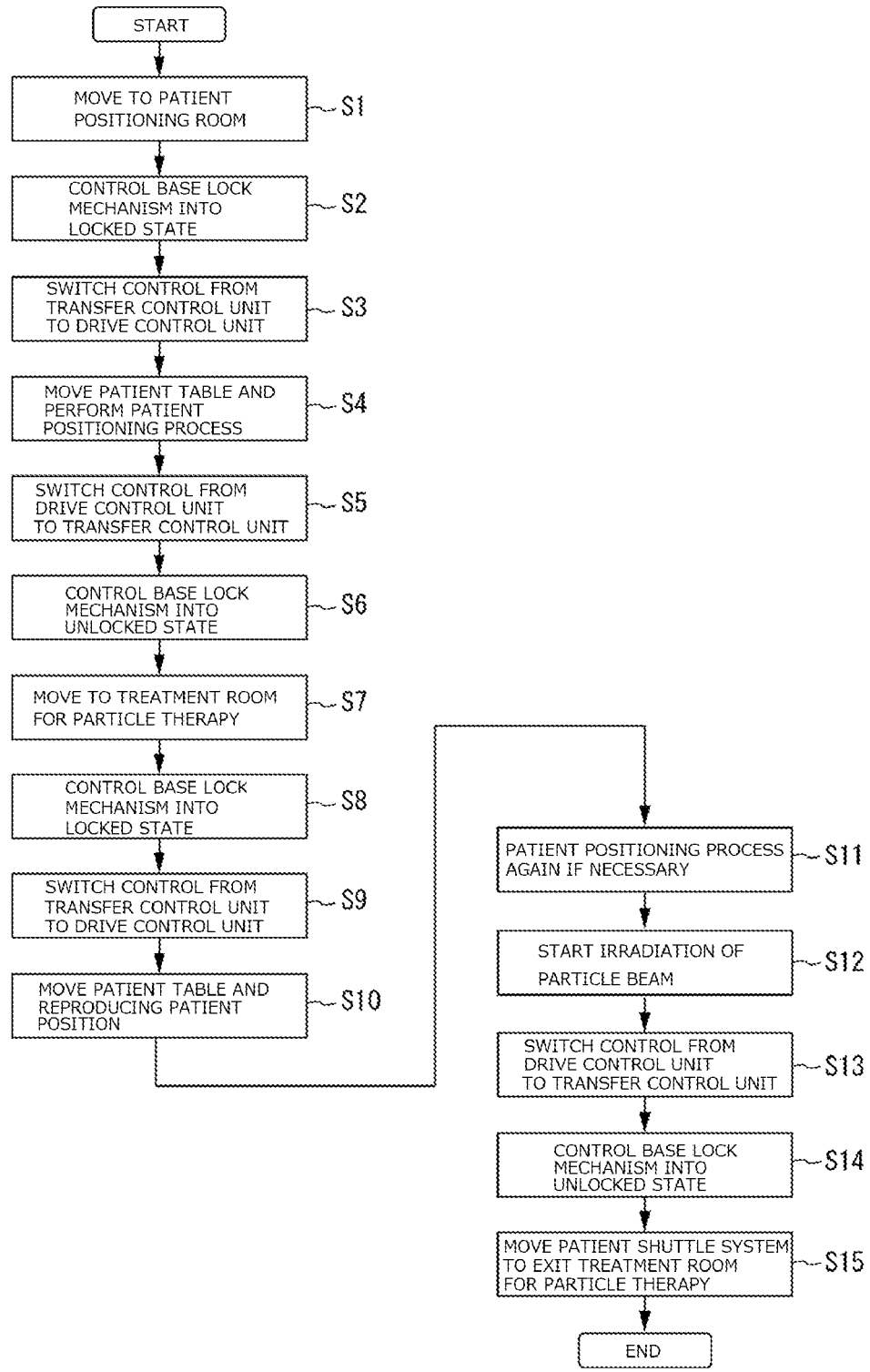
FIG. 10 is a flowchart illustrating a series of flows of particle therapy using the irradiation system for particle therapy.

FIG. 10 is a flowchart illustrating a series of flows of particle therapy in the irradiation system for particle therapy 200. Note that the order of steps in this flowchart is not limited to that in FIG. 10 and may be suitably adjusted if necessary.

Prior to particle therapy, a patient who has come to a facility of a hospital gets on the patient shuttle system 100 in a preparation room or the like and is secured to the patient table 110 by an immobilization device so as not to move. When a patient is getting on the patient table 110, the drive control unit 133 moves the patient table drive unit 120 to move the patient table 110 closer to the floor to make it easier for the patient to get on the patient table 110 (FIG. 2a). The patient table 110 on which the patient is placed returns to the home position state, and preparation for motion of the patient shuttle system 100 is completed.

A signal indicating that the preparation for motion is completed is transmitted from the transfer control unit 134 to the navigation controller 260, and the traffic management unit 262 of the navigation controller 260 transmits an instruction (including specifying of a path) to the transfer control unit 134 of the patient shuttle system 100. In response thereto, the drive control unit 133 enters a standby state, and the transfer control unit 134 moves the patient shuttle system 100 to a specified patient positioning room along the specified path (step S1).

In the patient positioning room, the transfer control unit 134 controls the base lock mechanism 137 into the locked state and transmits a signal indicating the completion of the lock to the patient positioning room management device 240 (step S2). In response thereto, the patient positioning room management device 240 transmits an instruction for controlling the transfer control unit 134 into a standby state and an instruction for recovering the drive control unit 133 from the standby state (step S3). The drive control unit 133 moves the patient table 110 and the patient table drive unit 120 to perform positioning of the particle beam irradiation position (step S4). Positioning data is transmitted from the patient positioning room management device 240 to the treatment room management device 250 via the network 270.

In response to completion of the positioning, the patient positioning room management device 240 transmits a signal for recovery to the home position of the drive unit 120 to the drive control unit 133, and in response thereto, the drive control unit 133 returns the patient table 110 to the home position state. The drive control unit 133 then transmits a signal indicating the recovery to the home position state to the patient positioning room management device 240, and the patient positioning room management device 240 transmits an instruction for recovering the transfer control unit 134 from the standby state and an instruction for controlling the drive control unit 133 into the standby state. In response thereto, the drive control unit 133 enters the standby state, and the transfer control unit 134 recovers from the standby state (step S5). The transfer control unit 134 controls the base lock mechanism 137 into the unlocked state (step S6).

The transfer control unit 134 transmits a signal indicating the establishment of the unlocked state to the patient positioning room management device 240, and the patient positioning room management device 240 that has received the signal transmits, to the navigation controller 260, an instruction for permitting the patient shuttle system 100 to move. In response thereto, the transfer control unit 134 moves the patient shuttle system 100 to a treatment room for particle therapy along a path specified by the navigation controller 260 (step S7).

In the treatment room for particle therapy, the transfer control unit 134 controls the base lock mechanism 137 into a locked state and transmits a signal indicating the establishment of the locked state to the treatment room management device 250 (step S8). In response thereto, the treatment room management device 250 transmits an instruction for controlling the transfer control unit 134 into a standby state and an instruction for recovering the drive control unit 133 from the standby state. In response thereto, the transfer control unit 134 enters the standby state, and the drive control unit 133 recovers from the standby state and is ready to control the patient table 110 and the patient table drive unit 120 (step S9). The drive control unit 133 receives information on the particle beam irradiation position determined in the patient positioning room from the treatment room management device 250 (including three-dimensional position and posture information on the patient table 110 and the patient table drive unit 120) and reproduces the patient position based on the information (step S10). Then, if necessary, a patient positioning process (step S11) may be further performed by the patient positioning device 230 in the treatment room for particle therapy.

In response to completion of the patient positioning, the navigation controller 260 actuates the particle beam irradiation apparatus 210 to start particle therapy (step S12).

In response to completion of the particle therapy, the treatment room management device 250 transmits a signal indicating the completion of the particle therapy to the drive control unit 133, and in response thereto, the drive control unit 133 returns the patient table 110 to the home position state. The treatment room management device 250 transmits an instruction for recovering the transfer control unit 134 from the standby state and an instruction for controlling the drive control unit 133 into a standby state. In response thereto, the drive control unit 133 enters the standby state, and the transfer control unit 134 recovers from the standby state (step S13). The transfer control unit 134 then controls the base lock mechanism 137 into the unlocked state (step S14). The transfer control unit 134 transmits a signal indicating the establishment of the unlocked state to the treatment room management device 250, and the treatment room management device 250 that has received this signal transmits, to the transfer control unit 134, an instruction for permitting the patient shuttle system 100 to move. In response thereto, the transfer control unit 134 causes the patient shuttle system 100 to start moving, exit the treatment room for particle therapy, and move to the preparation room or the like (step S15).

The features of the size, the material, the shape, the relative position of components, or the like described in the above embodiments may be arbitrary, and those skilled in the art would understand that such features may be changed in accordance with the structure of the apparatus to which the present invention is applied or various conditions. Further, the present invention is not limited to the embodiments specifically described above.

The present application is based on and claims priority from Japanese Patent Application No. 2021-38059, filed Mar. 10, 2021, the disclosure of which is hereby incorporated by reference herein in its entirety.

LIST OF REFERENCE SYMBOLS 100 patient shuttle system
110 patient table
120 patient table drive unit
121 first rotating mechanism
122 second rotating mechanism
123 third rotating mechanism
124 first arm
125 second arm
126 robot arm base
130 transfer unit
131 base
132 wheel
133 drive control unit
134 transfer control unit
135 helper space
136 sensor
137 base lock mechanism
138 recess
200 irradiation system for particle therapy
210 particle beam irradiation apparatus
220, 230 patient positioning device
240 patient positioning room management device
250 treatment room management device
260 navigation controller
270 network

What is claimed is:

1. A mobile patient shuttle system comprising:
a patient table adapted to carry a patient;
a patient table drive unit that moves and/or rotates the patient table; and
a transfer unit having a wheeled base on which the patient table drive unit is placed;
wherein the patient table drive unit comprises
a first rotating mechanism connected to the patient table and configured to rotate the patient table,
a first arm connected to the first rotating mechanism,
a second rotating mechanism connected to the first arm and configured to rotate the first arm,
a second arm connected to the second rotating mechanism,
a third rotating mechanism connected to the second arm and configured to rotate the second arm, and
a robot arm base connected to the third rotating mechanism,
wherein in a home position state of the patient shuttle system, the first rotating mechanism, the first arm, the second rotating mechanism, the second arm, the third rotating mechanism, and the robot arm base are configured to overlap the patient table in a height direction (Z-axis) such that the patient table, the first arm, and the second arm are in a folded state in the height direction (Z-axis),
wherein the robot arm base is fixed at a position offset from the center of the base, as seen in a top-down plan view, in order to secure, on the base, a helper space where a helper is able to ride during movement and relocation of said mobile patient shuttle system, and
wherein the robot arm base is fixed in a recess provided in the base.

2. The mobile patient shuttle system according to claim 1, wherein rotation about the Z-axis is defined as yaw rotation, an X-axis and a Y-axis orthogonal to each other are defined on a plane perpendicular to the Z-axis, rotation about the X-axis is defined as roll rotation, and rotation about the Y-axis is defined as pitch rotation,
wherein the first rotating mechanism is configured to apply roll rotation, pitch rotation, and yaw rotation to the patient table, wherein the second rotating mechanism is configured to apply roll rotation and yaw rotation to the first arm, and wherein the third rotating mechanism is configured to apply roll rotation and yaw rotation to the second arm.

3. The mobile patient shuttle system according to claim 1, wherein said wheeled base comprises three or more wheels mounted to the base, and wherein said wheels are omni-directional drive wheels.

4. A irradiation system for particle therapy comprising:
the mobile patient shuttle system according to claim 1;
a particle beam irradiation apparatus adapted to irradiate a patient with a particle beam; and
a navigation controller that controls traveling of the mobile patient shuttle system,
wherein the navigation controller includes
a path planning unit that plans a plurality of paths connecting a start point to an end point in a facility in which the irradiation system for particle therapy is provided, and
a traffic management unit that instructs the mobile patient shuttle system to move on a path selected from a plurality of paths planned by the path planning unit.

5. The irradiation system for particle therapy according to claim 4,
wherein the transfer unit further has a sensor,
wherein while moving on a path instructed by the navigation controller, the mobile patient shuttle system acquires, from the sensor, information on a space including the path and transmits, to the navigation controller, position information on the mobile patient shuttle system calculated by matching the information on the space with known map information,
wherein while moving on the path, the mobile patient shuttle system transmits a detection signal to the navigation controller in response to the sensor detecting an obstacle, and
wherein the traffic management unit of the navigation controller instructs the mobile patient shuttle system to move on another path selected from a plurality of paths planned by the path planning unit.

6. The irradiation system for particle therapy according to claim 4,
wherein the start point is a patient positioning room in the facility, and the end point is a treatment room for particle therapy in the facility, and
wherein the mobile patient shuttle system moves from the patient positioning room to the treatment room for particle therapy while maintaining the home position state.

7. The irradiation system for particle therapy according to claim 4,
wherein the irradiation system for particle therapy further includes
a patient positioning device and a patient positioning device provided in a patient positioning room and a treatment room for particle therapy of the facility, respectively, for positioning of an affected part of a patient relative to an isocenter of the particle beam,
a patient positioning room management device that manages the patient positioning device in the patient positioning room and the mobile patient shuttle system that entered the patient positioning room, and
a treatment room management device that manages the patient positioning device in the treatment room for particle therapy and the mobile patient shuttle system that entered the treatment room for particle therapy,
wherein the patient positioning room management device and the treatment room management device share, via a network, patient positioning data generated by using the patient positioning device of the patient positioning room and the patient positioning device of the treatment room for particle therapy,
wherein the mobile patient shuttle system further comprises a base lock mechanism that engages with lock receiving parts provided in the patient positioning room and the treatment room for particle therapy, respectively, to fix the mobile patient shuttle system to the patient positioning room and the treatment room for particle therapy,
wherein when the base lock mechanism engages with each of the lock receiving parts, the transfer unit enters a standby state, and the patient table drive unit recovers from a standby state, and
wherein when the base lock mechanism releases engagement with each of the lock receiving parts, the transfer unit recovers from a standby state, and the patient table drive unit enters a standby state.

8. The irradiation system for particle therapy according to claim 6,
wherein the irradiation system for particle therapy further includes
a patient positioning device and a patient positioning device provided in a patient positioning room and a treatment room for particle therapy of the facility, respectively, for positioning of an affected part of a patient relative to an isocenter of the particle beam,
a patient positioning room management device that manages the patient positioning device in the patient positioning room and the mobile patient shuttle system that entered the patient positioning room, and
a treatment room management device that manages the patient positioning device in the treatment room for particle therapy and the mobile patient shuttle system that entered the treatment room for particle therapy,
wherein the patient positioning room management device and the treatment room management device share, via a network, patient positioning data generated by using the patient positioning device of the patient positioning room and the patient positioning device of the treatment room for particle therapy,
wherein the mobile patient shuttle system further comprises a base lock mechanism that engages with lock receiving parts provided in the patient positioning room and the treatment room for particle therapy, respectively, to fix the mobile patient shuttle system to the patient positioning room and the treatment room for particle therapy,
wherein when the base lock mechanism engages with each of the lock receiving parts, the transfer unit enters a standby state, and the patient table drive unit recovers from a standby state, and
wherein when the base lock mechanism releases engagement with each of the lock receiving parts, the transfer unit recovers from a standby state, and the patient table drive unit enters a standby state.

9. The irradiation system for particle therapy according to claim 7, wherein during particle beam irradiation, in response to receiving an error signal from the patient table drive unit and/or the transfer unit, the treatment room management device transmits a signal to the particle beam irradiation apparatus to stop irradiation of a particle beam from the particle beam irradiation apparatus.

* * * * *